(12) United States Patent
Parent

(10) Patent No.: US 7,435,447 B2
(45) Date of Patent: Oct. 14, 2008

(54) METHOD AND SYSTEM FOR DETERMINING FLOW CONDITIONS IN A HIGH PRESSURE PROCESSING SYSTEM

(75) Inventor: Wayne M. Parent, Gilbert, AZ (US)

(73) Assignee: Tokyo Electron Limited, Tokyo (JP)

( * ) Notice: Subject to any disclaimer, the term of this patent is extended or adjusted under 35 U.S.C. 154(b) by 429 days.

(21) Appl. No.: 11/058,327

(22) Filed: Feb. 15, 2005

(65) Prior Publication Data

US 2006/0180175 A1   Aug. 17, 2006

(51) Int. Cl.
*B05D 3/12* (2006.01)

(52) U.S. Cl. .............. 427/345; 427/299; 427/427.2; 134/18; 134/108

(58) Field of Classification Search .......... 134/18, 134/56 R, 10, 108; 118/50, 688, 61, 602; 427/299, 345, 427.2

See application file for complete search history.

(56) References Cited

U.S. PATENT DOCUMENTS

| | | | |
|---|---|---|---|
| 2,617,719 A | 11/1952 | Stewart | 23/312 |
| 2,625,886 A | 1/1953 | Browne | 103/150 |
| 3,744,660 A | 7/1973 | Gaines et al. | 220/10 |
| 3,968,885 A | 7/1976 | Hassan et al. | 214/1 BC |
| 4,029,517 A | 6/1977 | Rand | 134/11 |
| 4,091,643 A | 5/1978 | Zucchini | 68/18 C |
| 4,245,154 A | 1/1981 | Uehara et al. | 250/227 |
| 4,341,592 A | 7/1982 | Shortes et al. | 156/643 |
| 4,355,937 A | 10/1982 | Mack et al. | 414/217 |
| 4,367,140 A | 1/1983 | Wilson | 210/110 |
| 4,406,596 A | 9/1983 | Budde | 417/393 |
| 4,422,651 A | 12/1983 | Platts | 277/206 R |
| 4,474,199 A | 10/1984 | Blaudszun | 134/105 |
| 4,522,788 A | 6/1985 | Sitek et al. | 422/78 |
| 4,549,467 A | 10/1985 | Wilden et al. | 91/307 |
| 4,592,306 A | 6/1986 | Gallego | 118/719 |
| 4,601,181 A | 7/1986 | Privat | 68/18 C |
| 4,626,509 A | 12/1986 | Lyman | 435/287 |

(Continued)

FOREIGN PATENT DOCUMENTS

CH   SE 251213   8/1948

(Continued)

OTHER PUBLICATIONS

J. B. Rubin et al., *A Comparison of Chilled DI Water/Ozone and $CO_2$-based Supercritical Fluids as Replacements for Photoresist-Stripping Solvents*, IEEE/CPMT Int'l Electronics Manufacturing Technology Symposium, pp. 308-314, 1998.

(Continued)

*Primary Examiner*—George R Koch, III
(74) *Attorney, Agent, or Firm*—Wood, Herron & Evans, L.L.P.

(57) ABSTRACT

In a high pressure processing system configured to treat a substrate, a flow measurement device is utilized to determine a flow condition in the high pressure processing system. The flow measurement device can, for example, comprise a turbidity meter. The flow parameter can, for example, include a volume flow rate or a time to achieve mixing of a process chemistry within a high pressure fluid used to treat the substrate.

16 Claims, 7 Drawing Sheets

U.S. PATENT DOCUMENTS

| | | | |
|---|---|---|---|
| 4,670,126 A | 6/1987 | Messer et al. | 204/298 |
| 4,682,937 A | 7/1987 | Credle, Jr. | 417/393 |
| 4,693,777 A | 9/1987 | Hazano et al. | 156/345 |
| 4,749,440 A | 6/1988 | Blackwood et al. | 156/646 |
| 4,778,356 A | 10/1988 | Hicks | 417/397 |
| 4,788,043 A | 11/1988 | Kagiyama et al. | 422/292 |
| 4,789,077 A | 12/1988 | Noe | 220/319 |
| 4,823,976 A | 4/1989 | White, III et al. | 220/211 |
| 4,825,808 A | 5/1989 | Takahashi et al. | 118/719 |
| 4,827,867 A | 5/1989 | Takei et al. | 118/64 |
| 4,838,476 A | 6/1989 | Rahn | 228/180.1 |
| 4,865,061 A | 9/1989 | Fowler et al. | 134/108 |
| 4,879,431 A | 11/1989 | Bertoncini | 435/311 |
| 4,917,556 A | 4/1990 | Stark et al. | 414/217 |
| 4,924,892 A | 5/1990 | Kiba et al. | 134/123 |
| 4,944,837 A | 7/1990 | Nishikawa et al. | 156/646 |
| 4,951,601 A | 8/1990 | Maydan et al. | 118/719 |
| 4,960,140 A | 10/1990 | Ishijima et al. | 134/31 |
| 4,983,223 A | 1/1991 | Gessner | 134/25.4 |
| 5,011,542 A | 4/1991 | Weil | 134/38 |
| 5,013,366 A | 5/1991 | Jackson et al. | 134/1 |
| 5,044,871 A | 9/1991 | Davis et al. | 414/786 |
| 5,062,770 A | 11/1991 | Story et al. | 417/46 |
| 5,068,040 A | 11/1991 | Jackson | 210/748 |
| 5,071,485 A | 12/1991 | Matthews et al. | 134/2 |
| 5,105,556 A | 4/1992 | Kurokawa et al. | 34/12 |
| 5,143,103 A | 9/1992 | Basso et al. | 134/98.1 |
| 5,167,716 A | 12/1992 | Boitnott et al. | 118/719 |
| 5,169,296 A | 12/1992 | Wilden | 417/395 |
| 5,169,408 A | 12/1992 | Biggerstaff et al. | 29/25.01 |
| 5,185,296 A | 2/1993 | Morita et al. | 437/229 |
| 5,186,594 A | 2/1993 | Toshima et al. | 414/217 |
| 5,186,718 A | 2/1993 | Tepman et al. | 29/25.01 |
| 5,188,515 A | 2/1993 | Horn | 417/63 |
| 5,190,373 A | 3/1993 | Dickson et al. | 366/146 |
| 5,191,993 A | 3/1993 | Wanger et al. | 220/333 |
| 5,193,560 A | 3/1993 | Tanaka et al. | 134/56 R |
| 5,195,878 A | 3/1993 | Sahiavo et al. | 417/393 |
| 5,213,485 A | 5/1993 | Wilden | 417/393 |
| 5,213,619 A | 5/1993 | Jackson et al. | 134/1 |
| 5,215,592 A | 6/1993 | Jackson | 134/1 |
| 5,217,043 A | 6/1993 | Novakovi | 137/460 |
| 5,221,019 A | 6/1993 | Pechacek et al. | 220/315 |
| 5,222,876 A | 6/1993 | Budde | 417/393 |
| 5,224,504 A | 7/1993 | Thompson et al. | 134/155 |
| 5,236,602 A | 8/1993 | Jackson | 210/748 |
| 5,236,669 A | 8/1993 | Simmons et al. | 422/113 |
| 5,237,824 A | 8/1993 | Pawliszyn | 62/51.1 |
| 5,240,390 A | 8/1993 | Kvinge et al. | 417/393 |
| 5,243,821 A | 9/1993 | Schuck et al. | 62/50.6 |
| 5,246,500 A | 9/1993 | Samata et al. | 118/719 |
| 5,251,776 A | 10/1993 | Morgan, Jr. et al. | 220/360 |
| 5,267,455 A | 12/1993 | Dewees et al. | 68/5 C |
| 5,280,693 A | 1/1994 | Heudecker | 53/306 |
| 5,285,352 A | 2/1994 | Pastore et al. | 361/707 |
| 5,288,333 A | 2/1994 | Tanaka et al. | 134/31 |
| 5,304,515 A | 4/1994 | Morita et al. | 437/231 |
| 5,306,350 A | 4/1994 | Hoy et al. | 134/22.14 |
| 5,313,965 A | 5/1994 | Palen | 134/61 |
| 5,314,574 A | 5/1994 | Takahashi | 156/646 |
| 5,316,591 A | 5/1994 | Chao et al. | 134/34 |
| 5,328,722 A | 7/1994 | Ghanayem et al. | 427/250 |
| 5,337,446 A | 8/1994 | Smith et al. | 15/21.1 |
| 5,339,844 A | 8/1994 | Stanford, Jr. et al. | 134/107 |
| 5,355,901 A | 10/1994 | Mielnik et al. | 134/105 |
| 5,368,171 A | 11/1994 | Jackson | 134/147 |
| 5,370,740 A | 12/1994 | Chao et al. | 134/1 |
| 5,370,741 A | 12/1994 | Bergman | 134/3 |
| 5,377,705 A | 1/1995 | Smith, Jr. et al. | 134/95.3 |
| 5,401,322 A | 3/1995 | Marshall | 134/13 |
| 5,403,621 A | 4/1995 | Jackson et al. | 427/255.1 |
| 5,404,894 A | 4/1995 | Shiraiwa | 134/66 |
| 5,412,958 A | 5/1995 | Iliff et al. | 68/5 C |
| 5,417,768 A | 5/1995 | Smith, Jr. et al. | 134/10 |
| 5,433,334 A | 7/1995 | Reneau | 220/319 |
| 5,447,294 A | 9/1995 | Sakata et al. | 266/257 |
| 5,456,759 A | 10/1995 | Stanford, Jr. et al. | 134/1 |
| 5,494,526 A | 2/1996 | Paranjpe | 134/1 |
| 5,500,081 A | 3/1996 | Bergman | 156/646.1 |
| 5,501,761 A | 3/1996 | Evans et al. | 156/344 |
| 5,503,176 A | 4/1996 | Dunmire et al. | 137/15 |
| 5,505,219 A | 4/1996 | Lansberry et al. | 134/105 |
| 5,509,431 A | 4/1996 | Smith, Jr. et al. | 134/95.1 |
| 5,522,938 A | 6/1996 | O'Brien | 134/1 |
| 5,526,834 A | 6/1996 | Mielnik et al. | 134/105 |
| 5,533,538 A | 7/1996 | Marshall | 134/104.4 |
| 5,571,330 A | 11/1996 | Kyogoku | 118/719 |
| 5,589,224 A | 12/1996 | Tepman et al. | 427/248.1 |
| 5,621,982 A | 4/1997 | Yamashita et al. | 34/203 |
| 5,629,918 A | 5/1997 | Ho et al. | 369/112 |
| 5,644,855 A | 7/1997 | McDermott et al. | 34/516 |
| 5,649,809 A | 7/1997 | Stapelfeldt | 417/63 |
| 5,656,097 A | 8/1997 | Olesen et al. | 134/1 |
| 5,669,251 A | 9/1997 | Townsend et al. | 68/58 |
| 5,672,204 A | 9/1997 | Habuka | 117/204 |
| 5,683,977 A | 11/1997 | Jureller et al. | 510/286 |
| 5,702,228 A | 12/1997 | Tamai et al. | 414/744.5 |
| 5,706,319 A | 1/1998 | Holtz | 376/203 |
| 5,746,008 A | 5/1998 | Yamashita et al. | 34/211 |
| 5,769,588 A | 6/1998 | Toshima et al. | 414/217 |
| 5,797,719 A | 8/1998 | James et al. | 417/46 |
| 5,798,126 A | 8/1998 | Fujikawa et al. | 425/78 |
| 5,817,178 A | 10/1998 | Mita et al. | 118/666 |
| 5,868,856 A | 2/1999 | Douglas et al. | 134/2 |
| 5,868,862 A | 2/1999 | Douglas et al. | 134/26 |
| 5,881,577 A | 3/1999 | Sauer et al. | 68/5 |
| 5,882,165 A | 3/1999 | Maydan et al. | 414/217 |
| 5,888,050 A | 3/1999 | Fitzgerald et al. | 417/46 |
| 5,898,727 A | 4/1999 | Fujikawa et al. | 373/110 |
| 5,900,107 A | 5/1999 | Murphy et al. | 156/359 |
| 5,900,354 A | 5/1999 | Batchelder | 430/395 |
| 5,904,737 A | 5/1999 | Preston et al. | 8/158 |
| 5,906,866 A | 5/1999 | Webb | 427/534 |
| 5,908,510 A | 6/1999 | McCullough et al. | 134/2 |
| 5,928,389 A | 7/1999 | Jevtic | 29/25.01 |
| 5,932,100 A | 8/1999 | Yager et al. | 210/634 |
| 5,934,856 A | 8/1999 | Asakawa et al. | 414/217 |
| 5,934,991 A | 8/1999 | Rush | 454/187 |
| 5,955,140 A | 9/1999 | Smith et al. | 427/96 |
| 5,975,492 A | 11/1999 | Brenes | 251/175 |
| 5,976,264 A | 11/1999 | McCullough et al. | 134/2 |
| 5,979,306 A | 11/1999 | Fujikawa et al. | 100/90 |
| 5,980,648 A | 11/1999 | Adler | 134/34 |
| 5,981,399 A | 11/1999 | Kawamura et al. | 438/715 |
| 5,989,342 A | 11/1999 | Ikeda et al. | 118/52 |
| 6,005,226 A | 12/1999 | Aschner et al. | 219/390 |
| 6,017,820 A | 1/2000 | Ting et al. | 438/689 |
| 6,024,801 A | 2/2000 | Wallace et al. | 134/1 |
| 6,029,371 A | 2/2000 | Kamikawa et al. | 34/516 |
| 6,035,871 A | 3/2000 | Eui-Yeol | 134/61 |
| 6,037,277 A | 3/2000 | Masakara et al. | 438/787 |
| 6,053,348 A | 4/2000 | Morch | 220/263 |
| 6,056,008 A | 5/2000 | Adams et al. | 137/487.5 |
| 6,067,728 A | 5/2000 | Farmer et al. | 34/470 |
| 6,077,053 A | 6/2000 | Fujikawa et al. | 417/399 |
| 6,077,321 A | 6/2000 | Adachi et al. | 29/25.01 |
| 6,082,150 A | 7/2000 | Stucker | 68/18 R |
| 6,085,935 A | 7/2000 | Malchow et al. | 220/813 |
| 6,097,015 A | 8/2000 | McCullough et al. | 219/686 |
| 6,110,232 A | 8/2000 | Chen et al. | 29/25.01 |
| 6,122,566 A | 9/2000 | Nguyen et al. | 700/218 |
| 6,128,830 A | 10/2000 | Bettcher et al. | 34/404 |
| 6,145,519 A | 11/2000 | Konishi et al. | 134/95.2 |
| 6,149,828 A | 11/2000 | Vaartstra | 216/57 |

| | | | |
|---|---|---|---|
| 6,159,295 A | 12/2000 | Maskara et al. ............ 118/688 |
| 6,164,297 A | 12/2000 | Kamikawa .................. 134/61 |
| 6,186,722 B1 | 2/2001 | Shirai ........................ 414/217 |
| 6,203,582 B1 | 3/2001 | Berner et al. ............. 29/25.01 |
| 6,216,364 B1 | 4/2001 | Tanaka et al. ................ 34/448 |
| 6,228,563 B1 | 5/2001 | Starov et al. ............... 430/327 |
| 6,235,634 B1 | 5/2001 | White et al. ............... 438/680 |
| 6,239,038 B1 | 5/2001 | Wen ........................... 438/745 |
| 6,241,825 B1 | 6/2001 | Wytman ..................... 118/733 |
| 6,242,165 B1 | 6/2001 | Vaartstra .................... 430/329 |
| 6,244,121 B1 | 6/2001 | Hunter ..................... 73/865.9 |
| 6,251,250 B1 | 6/2001 | Keigler ......................... 205/89 |
| 6,277,753 B1 | 8/2001 | Mullee et al. .............. 438/692 |
| 6,286,231 B1 | 9/2001 | Bergman et al. ............. 34/410 |
| 6,305,677 B1 | 10/2001 | Lenz ............................ 269/13 |
| 6,306,564 B1 | 10/2001 | Mullee |
| 6,319,858 B1 | 11/2001 | Lee et al. .................... 438/787 |
| 6,334,266 B1 | 1/2002 | Moritz et al. ................. 34/337 |
| 6,344,174 B1 | 2/2002 | Miller et al. .................. 422/98 |
| 6,355,072 B1 | 3/2002 | Racette et al. ................. 8/142 |
| 6,388,317 B1 | 5/2002 | Reese ......................... 257/713 |
| 6,389,677 B1 | 5/2002 | Lenz ........................... 29/559 |
| 6,418,956 B1 | 7/2002 | Bloom ....................... 137/14 |
| 6,436,824 B1 | 8/2002 | Chooi et al. ................ 438/687 |
| 6,454,519 B1 | 9/2002 | Toshima et al. ............ 414/805 |
| 6,454,945 B1 | 9/2002 | Weigl et al. ................. 210/634 |
| 6,464,790 B1 | 10/2002 | Sherstinsky et al. ......... 118/715 |
| 6,508,259 B1 | 1/2003 | Tseronis et al. ............ 134/105 |
| 6,509,141 B2 | 1/2003 | Mullee |
| 6,521,466 B1 | 2/2003 | Castrucci ....................... 438/5 |
| 6,541,278 B2 | 4/2003 | Morita et al. .................. 438/3 |
| 6,546,946 B2 | 4/2003 | Dunmire ................. 137/15.18 |
| 6,550,484 B1 | 4/2003 | Gopinath et al. ............ 134/1.2 |
| 6,558,475 B1 | 5/2003 | Simons et al. ................ 134/21 |
| 6,561,213 B2 | 5/2003 | Wang et al. ................. 137/263 |
| 6,561,220 B2 | 5/2003 | McCullough et al. .. 137/565.12 |
| 6,561,481 B1 | 5/2003 | Filonczuk .............. 251/129.12 |
| 6,561,767 B2 | 5/2003 | Berger et al. ................. 417/53 |
| 6,564,826 B2 | 5/2003 | Shen ...................... 137/505.18 |
| 6,802,961 B2 | 10/2004 | Jackson ....................... 210/86 |
| 6,890,853 B2 | 5/2005 | Biberger et al. ............. 438/670 |
| 2002/0046707 A1 | 4/2002 | Biberger et al. |
| 2003/0198895 A1 | 10/2003 | Toma et al. |
| 2004/0020518 A1 | 2/2004 | DeYoung et al. ............... 134/30 |
| 2004/0112409 A1 | 6/2004 | Schilling |
| 2004/0177867 A1 | 9/2004 | Schilling |
| 2005/0077597 A1 | 4/2005 | Toma et al. |
| 2006/0065189 A1* | 3/2006 | Babic et al. .................... 118/50 |

FOREIGN PATENT DOCUMENTS

| | | |
|---|---|---|
| DE | 36 08 783 A1 | 9/1987 |
| DE | 39 04 514 C2 | 3/1990 |
| DE | 40 04 111 C2 | 8/1990 |
| DE | 39 06 724 C2 | 9/1990 |
| DE | 39 06 735 C2 | 9/1990 |
| DE | 39 06 737 A1 | 9/1990 |
| DE | 44 29 470 A1 | 3/1995 |
| DE | 43 44 021 A1 | 6/1995 |
| DE | 198 60 084 A1 | 7/2000 |
| EP | 0 244 951 A2 | 11/1987 |
| EP | 02 72 141 A2 | 6/1988 |
| EP | 0 283 740 A2 | 9/1988 |
| EP | 0 302 345 A2 | 2/1989 |
| EP | 0 370 233 A1 | 5/1990 |
| EP | 0 391 035 A2 | 10/1990 |
| EP | 0 453 867 A1 | 10/1991 |
| EP | 0 518 653 B1 | 12/1992 |
| EP | 0 536 752 A2 | 4/1993 |
| EP | 0 572 913 A1 | 12/1993 |
| EP | 0 587 168 A1 | 3/1994 |
| EP | 0 620 270 A3 | 10/1994 |
| EP | 0 679 753 B1 | 11/1995 |
| EP | 0 711 864 B1 | 5/1996 |
| EP | 0 726 099 A2 | 8/1996 |
| EP | 0 822 583 A2 | 2/1998 |
| EP | 0 829 312 A2 | 3/1998 |
| EP | 0 836 895 A2 | 4/1998 |
| EP | 0 903 775 A2 | 3/1999 |
| FR | 1 499 491 | 9/1967 |
| GB | 2 003 975 | 3/1979 |
| GB | 2 193 482 | 2/1988 |
| JP | 60-192333 | 9/1985 |
| JP | 60-2348479 | 11/1985 |
| JP | 60-246635 | 12/1985 |
| JP | 61-017151 | 1/1986 |
| JP | 61-231166 | 10/1986 |
| JP | 62-125619 | 6/1987 |
| JP | 63-303059 | 12/1988 |
| JP | 1-246835 | 10/1989 |
| JP | 2-148841 | 6/1990 |
| JP | 2-209729 | 8/1990 |
| JP | 2-304941 | 12/1990 |
| JP | 7-142333 | 6/1995 |
| JP | 8-186140 A | 7/1996 |
| JP | 10-144757 A | 5/1998 |
| JP | 56-142629 | 11/1998 |
| JP | 10335408 A | 12/1998 |
| JP | 11-200035 | 7/1999 |
| JP | 2000-106358 | 4/2000 |
| WO | WO 87/07309 | 12/1987 |
| WO | WO 90/06189 | 6/1990 |
| WO | WO 90/13675 | 11/1990 |
| WO | WO 91/12629 A | 8/1991 |
| WO | WO 93/14255 | 7/1993 |
| WO | WO 93/14259 | 7/1993 |
| WO | WO 93/20116 | 10/1993 |
| WO | WO 96/27704 | 9/1996 |
| WO | WO 99/18603 A | 4/1999 |
| WO | WO 99/49998 | 10/1999 |
| WO | WO 00/36635 | 6/2000 |
| WO | WO 00/73241 A1 | 12/2000 |
| WO | WO 01/10733 A1 | 2/2001 |
| WO | WO 01/33615 A3 | 5/2001 |
| WO | WO 01/55628 A1 | 8/2001 |
| WO | WO 01/68279 A2 | 9/2001 |
| WO | WO 01/74538 A1 | 10/2001 |
| WO | WO 01/78911 A1 | 10/2001 |
| WO | WO 01/85391 A2 | 11/2001 |
| WO | WO 01/94782 A2 | 12/2001 |
| WO | WO 02/09894 A2 | 2/2002 |
| WO | WO 02/11191 A2 | 2/2002 |
| WO | WO 02/16051 A2 | 2/2002 |
| WO | WO 03/030219 A2 | 10/2003 |

OTHER PUBLICATIONS

J.B. Rubin et al., *Los Alamos National Laboratory*, Solid State Technology, pp. S10 & S14, Oct. 1998.

J.B. Rubin et al., *Supercritical Carbon Dioxide Resist Remover, SCORR, the Path to Least Photoresistance*, Los Alamos National Laboratory, 1998.

Z. Guan et al., *Fluorocarbon-Based Heterophase Polymeric Materials. I. Block Copolymer Surfactants for Carbon Dioxide Applications*, Macromolecules, vol. 27, pp. 5527-5532, 1994.

A. Guan et al., *International Journal of Environmentally Conscious Design & Manufacturing*, vol. 2, No. 1, pp. 83, 1993.

Matson and Smith, *Supercritical Fluids*, Journal of the American Ceramic Society, vol. 72, No. 6, pp. 872-874, no date.

D. H. Ziger et al., *Compressed Fluid Technology: Application to RIE Developed Resists*, AIChE Journal, vol. 33, No. 10, pp. 1585-1591, Oct. 1987.

Kirk-Othmer, *Alcohol Fuels to Toxicology*, Encyclopedia of Chemical Terminology, 3rd ed., Supplement vol., New York: John Wiley & Sons, pp. 872-893, 1984.

Kirk-Othmer, *Cleaning with Supercritical $CO_2$*, NASA Tech Briefs, MFS-29611, Marshall Space Flight Center, Alabama, Mar. 1979.

N. Basta, *Supercritical Fluids: Still Seeking Acceptance*, Chemical Engineering vol. 92, No. 3, pp. 14, Feb. 24, 1985.

D. Takahashi, *Los Alamos Lab Finds Way to Cut Chip Toxic Waste*, Wall Street Journal, Jun. 22, 1998.

D. Takahashi, *Supercritical $CO_2$ Process Offers Less Mess from Semiconductor Plants*, Chemical Engineering Magazine, pp. 27 & 29, Jul. 1988.

Y. P. Sun, *Preparation of Polymer Protected Semiconductor Nanoparticles Through the Rapid Expansion of Supercritical Fluid Solution*, Chemical Physics Letters, pp. 585-588, May 22, 1998.

K. Jackson et al., *Surfactants and Micromulsions in Supercritical Fluids*, Supercritical Fluid Cleaning, Noyes Publications, Westwood, NJ, pp. 87-120, Spring 1998.

M. Kryszcwski, *Production of Metal and Semiconductor Nanoparticles in Polymer Systems*, Polimery, pp. 65-73, Feb. 1998.

G. L. Bakker et al., *Surface Cleaning and Carbonaceous Film Removal Using High Pressure, High Temperature Water, and Water/$CO_2$ Mixtures*, J Electrochem Soc., vol. 145, No. 1, pp. 284-291, Jan. 1998.

C. K. Ober et al., *Imaging Polymers with Supercritical Carbon Dioxide*, Advanced Materials, vol. 9, No. 13, pp. 1039-1043, Nov. 3, 1997.

E. M. Russick et al., *Supercritical Carbon Dioxide Extraction of Solvent from Micro-Machined Structures*, Supercritical Fluids Extraction and Pollution Prevention, ACS Symposium Series, vol. 670, pp. 255-269, Oct. 21, 1997.

N. Dahmen et al., *Supercritical Fluid Extraction of Grinding and Metal Cutting Waste Contaminated with Oils*, Supercritical Fluids—Extraction and Pollution Prevention, ACS Symposium Series, vol. 670, pp. 270-279, Oct. 21, 1997.

C. M. Wai, *Supercritical Fluid Extraction: Metals as Complexes*, Journal of Chromatography A, vol. 785, pp. 369-383, Oct. 17, 1997.

C. Xu et al., *Submicron-Sized Spherical Yttrium Oxide Based Phosphors Prepared by Supercritical $CO_2$-Assisted Nerosolization and Pyrolysis*, Appl. Phys. Lett., vol. 71, No. 22, pp. 1643-1645, Sep. 22, 1997.

Y. Tomioka et al., *Decomposition of Tetramethylammonium (TMA) in a Positive Photo-resist Developer by Supercritical Water*, Abstracts of Papers 214th ACS Natl Meeting, American Chemical Society, Abstract No. 108, Sep. 7, 1997.

H. Klein et al., *Cyclic Organic Carbonates Serve as Solvents and Reactive Diluents*, Coatings World, pp. 38-40, May 1997.

J. Bühler et al., *Linear Array of Complementary Metal Oxide Semiconductor Double-Pass Metal Micro-mirrors*, Opt. Eng. vol. 36, No. 5, pp. 1391-1398, May 1997.

M. H. Jo et al., *Evaluation of $SiO_2$ Aerogel Thin Film with Ultra Low Dielectric Constant as an Intermetal Dielectric*, Micrelectronic Engineering, vol. 33, pp. 343-348, Jan. 1997.

J. B. McClain et al., *Design of Nonionic Surfactants for Supercritical Carbon Dioxide*, Science, vol. 274, pp. 2049-2052, Dec. 20, 1996.

L. Znaidi et al., *Batch and Semi-Continuous Synthesis of Magnesium Oxide Powders from Hydrolysis and Supercritical Treatment of $Mg(OCH_3)_2$*, Materials Research Bulletin, vol. 31, No. 12, pp. 1527-1535, Dec. 1996.

M. E. Tadros, *Synthesis of Titanium Dioxide Particles in Supercritical $CO_2$*, J. Supercritical Fluids, vol. 9, pp. 172-176, Sep. 1996.

V. G. Courtecuisse et al., *Kinetics of the Titanium Isopropoxide Decomposition in Supercritical Isopropyl Alcohol*, Ind. Eng. Chem. Res., vol. 35, No. 8, pp. 2539-2545, Aug. 1996.

A. Gabor et al., *Block and Random Copolymer Resists Designed for 193 nm Lithography and Environmentally Friendly Supercritical $CO_2$ Development*, SPIE, vol. 2724, pp. 410-417, Jun. 1996.

G. L. Schimek et al., *Supercritical Ammonia Synthesis and Characterization of Four New Alkali Metal Silver Antimony Sulfides . . .* , J. Solid State Chemistry, vol. 123, pp. 277-284, May 1996.

P. Gallagher-Wetmore et al., *Supercritical Fluid Processing: Opportunities for New Resist Materials and Processes*, SPIE, vol. 2725, pp. 289-299, Apr. 1996.

K. I. Papathomas et al., *Debonding of Photoresists by Organic Solvents*, J. Applied Polymer Science, vol. 59, pp. 2029-2037, Mar. 28, 1996.

J. J. Watkins et al., *Polymer/Metal Nanocomposite Synthesis in Supercritical $CO_2$*, Chemistry of Materials, vol. 7, No. 11, pp. 1991-1994, Nov. 1995.

E. F. Gloyna et al., *Supercritical Water Oxidation Research and Development Update*, Environmental Progress, vol. 14, No. 3, pp. 182-192, Aug. 1995.

P. Gallagher-Wetmore et al., *Supercritical Fluid Processing: A New Dry Technique for Photoresist Developing*, SPIE, vol. 2438, pp. 694-708, Jun. 1995.

A. H. Gabor et al., *Silicon-Containing Block Copolymer Resist Materials*, Microelectronics Technology—Polymers for Advanced Imaging and Packaging, ACS Symposium Series, vol. 615, pp. 281-298, Apr. 1995.

P. C. Tsiartas et al., *Effect of Molecular Weight Distribution on the Dissolution Properties of Novolac Blends*, SPIE, vol. 2438, pp. 264-271, Jun. 1995.

R. D. Allen et al., *Performance Properties of Near-Monodisperse Novolak Resins*, SPIE, vol. 2438, pp. 250-260, Jun. 1995.

P. T. Wood et al., *Synthesis of New Channeled Structures in Supercritical Amines . . .* , Inorg. Chem., vol. 33, pp. 1556-1558, 1994.

J. B. Jerome et al., *Synthesis of New Low-Dimensional Quaternary Compounds . . .* , Inorg. Chem., vol. 33, pp. 1733-1734, 1994.

J. McHardy et al., *Progress in Supercritical $CO_2$ Cleaning*, SAMPE Jour, vol. 29, No. 5, pp. 20-27, Sep. 1993.

R. Purtell et al., *Precision Parts Cleaning Using Supercritical Fluids*, J. Vac. Sci. Technol. A., vol. 11, No. 4, pp. 1696-1701, Jul. 1993.

E. Bok et al., *Supercritical Fluids for Single Wafer Cleaning*, Solid State Technology, pp. 117-120, Jun. 1992.

T. Adschiri et al., *Rapid and Continuous Hydrothermal Crystallization of Metal Oxide Particles in Supercritical Water*, J. Am. Ceram. Cos., vol. 75, No. 4, pp. 1019-1022, 1992.

B. N. Hansen et al., *Supercritical Fluid Transport—Chemical Deposition of Films*, Chem. Mater, vol. 4, No. 4, pp. 749-752, 1992.

S. H. Page et al., *Predictability and Effect of Phase Behavior of $CO_2$/Propylene Carbonate in Supercritical Fluid Chromatography*, J. Microcol, vol. 3, No. 4, pp. 355-369, 1991.

T. Brokamp et al., *Synthese und Kristallstruktur Eines Gemischtvalenten Lithium-Tantalnitride $Li_2Ta_3N_5$*, J. Alloys and Compounds, vol. 176, pp. 47-60, 1991.

B. M. Hybertson et al., *Deposition of Palladium Films by a Novel Supercritical Transport Chemical Deposition Process*, Mat. Res. Bull., vol. 26, pp. 1127-1133, 1991.

D. W. Matson et al., *Rapid Expansion of Supercritical Fluid Solutions: Solute Formation of Powders, Thin Films, and Fibers*, Ind. Eng. Chem. Res., vol. 26, No. 11, pp. 2298-2306, 1987.

W. K. Tolley et al., *Stripping Organics from Metal and Mineral Surfaces Using Supercritical Fluids*, Separation Science and Technology, vol. 22, pp. 1087-1101, 1987.

W.K. Tolley et al., *Final Report on the Safety Assessment of Propylene Carbonate*, J. American College of Toxicology, vol. 6, No. 1, pp. 23-51, 1987.

W.K. Tolley et al., *Porous Xerogel Films as Ultra-Low Permittivity Dielectrics for ULSI Interconnect Applications*, Materials Research Society, pp. 463-469, 1987.

Kawakami et al., *A Super Low-k(k=1.1) Silica Aerogel Film Using Supercritical Drying Technique*, IEEE, pp. 143-145, 2000.

R. F. Reidy, *Effects of Supercritical Processing on Ultra Low-k Films*, Texas Advanced Technology Program, Texas Instruments and the Texas Academy of Mathematics and Science, Oct. 1, 2002.

Anthony Muscat, *Backend Processing Using Supercritical $CO_2$*, University of Arizona, May 15, 2003.

D. Goldfarb et al., *Aqueous-based Photoresist Drying Using Supercritical Carbon Dioxide to Prevent Pattern Collapse*, J. Vacuum Sci. Tech. B, vol. 18, No. 6, pp. 3313, 2000.

H. Namatsu et al., *Supercritical Drying for Water-Rinsed Resist Systems*, J. Vacuum Sci. Tech. B, vol. 18, No. 6, pp. 3308, 2000.

N. Sundararajan et al., *Supercritical $CO_2$ Processing for Submicron Imaging of Fluoropolymers*, Chem. Mater., vol. 12, 41, 2000.

Hideaki Itakura et al., *Multi-Chamber Dry Etching System*, Solid State Technology, pp. 209-214, Apr. 1982.

Joseph L. Foszez, *Diaphragm Pumps Eliminate Seal Problems*, Plant Engineering, pp. 1-5, Feb. 1, 1996.

Bob Agnew, *Wilden Air-Operated Diaphragm Pumps*, Process & Industrial Training Technologies, Inc., 1996.

* cited by examiner

METHOD AND SYSTEM FOR DETERMINING FLOW CONDITIONS IN A HIGH PRESSURE PROCESSING SYSTEM

BACKGROUND OF THE INVENTION

1. Field of the Invention

The present invention relates to a method and system for determining a flow condition in a high pressure processing system configured to treat a substrate and, more particularly, to a method and system for maintaining fluid flow in a high pressure processing system.

2. Description of Related Art

During the fabrication of semiconductor devices for integrated circuits (ICs), a sequence of material processing steps, including both pattern etching and deposition processes, are performed, whereby material is removed from or added to a substrate surface, respectively. During, for instance, pattern etching, a pattern formed in a mask layer of radiation-sensitive material, such as photoresist, using for example photolithography, is transferred to an underlying thin material film using a combination of physical and chemical processes to facilitate the selective removal of the underlying material film relative to the mask layer.

Thereafter, the remaining radiation-sensitive material, or photoresist, and post-etch residue, such as hardened photoresist and other etch residues, are removed using one or more cleaning processes. Conventionally, these residues are removed by performing plasma ashing in an oxygen plasma, followed by wet cleaning through immersion of the substrate in a liquid bath of stripper chemicals.

Until recently, dry plasma ashing and wet cleaning were found to be sufficient for removing residue and contaminants accumulated during semiconductor processing. However, recent advancements for ICs include a reduction in the critical dimension for etched features below a feature dimension acceptable for wet cleaning, such as a feature dimension below approximately 45 to 65 nanometers (nm). Moreover, the advent of new materials, such as low dielectric constant (low-k) materials, limits the use of plasma ashing due to their susceptibility to damage during plasma exposure.

Therefore, at present, interest has developed for the replacement of dry plasma ashing and wet cleaning. One interest includes the development of dry cleaning systems utilizing a supercritical fluid as a carrier for a solvent, or other residue removing composition. At present, the inventor(s) have recognized that conventional dry cleaning systems are deficient in, for example, repeating the same flow conditions from one substrate to the next substrate. For instance, many dry cleaning systems lack the ability to avoid drifting process conditions, such as the variation of filter performance due to the accumulation of particles.

SUMMARY OF THE INVENTION

One objective of the invention is to provide a method and system for determining a flow condition in a high pressure processing system.

Another embodiment of the invention is to provide a method and system for measuring a flow condition in a high pressure processing system. In particular, flow rate, chemistry density or homogeneity, or other flow conditions can be measured using a coriolis meter, a turbidity meter or other flow condition measurement devices.

A further objective of the invention is to provide a method and system by which a flow condition of the fluid in a high pressure processing system, particularly a supercritical fluid processing system, can be maintained or controlled.

According to an embodiment of the invention, a high pressure processing system for treating a substrate is provided comprising: a processing chamber configured to treat the substrate; a platen coupled to the processing chamber and configured to support the substrate; a high pressure fluid supply system configured to introduce a high pressure fluid to the processing chamber; a fluid flow system coupled to the processing chamber and configured to flow the high pressure fluid over the substrate in the processing chamber; a process chemistry supply system having an injection system configured to introduce a process chemistry to the processing chamber; and a flow condition measurement device coupled to the fluid flow system and configured to output a signal related to a flow parameter for the high pressure fluid.

According to a further objective of the invention, the system is provided with a controller that is coupled to the flow measurement device and the fluid flow system and is configured to adjust a flow of the high pressure fluid in response to the output signal.

According to yet another embodiment, a method of treating a substrate is provided comprising: placing the substrate in a high pressure processing chamber onto a platen configured to support the substrate; forming a supercritical fluid from a fluid by adjusting a pressure of the fluid above the critical pressure of the fluid, and adjusting a temperature of the fluid above the critical temperature of the fluid; introducing the supercritical fluid to the high pressure processing chamber; introducing a process chemistry to the supercritical fluid; flowing the high pressure fluid and the process chemistry over the substrate; and determining a flow parameter related to the high pressure fluid using a flow measurement device.

According to a further embodiment of the invention, the apparatus of the invention is provided with a controller that controls the flow condition in response to the flow condition measurement, and in particular, controls the flow condition to maintain a uniform flow condition from wafer to wafer.

According to a still further embodiment of the invention, the method of the invention is provided in which the flow condition is controlled in response to the flow parameter determination, and in particular, to maintain the flow condition uniform from wafer to wafer.

Also provided according to another embodiment of the invention is a method of treating a substrate comprising: placing the substrate onto a platen configured to support the substrate in a processing chamber of a high pressure fluid processing system; introducing a high pressure fluid in the high pressure processing system; introducing a process chemistry to the high pressure fluid; flowing the high pressure fluid and the process chemistry over the substrate; determining a flow parameter of the high pressure fluid and the process chemistry using a flow condition measurement device; and adjusting a flow condition of the fluid in the processing system in response to the flow parameter determination.

DETAILED DESCRIPTION OF EXEMPLARY EMBODIMENTS

In the following description, to facilitate a thorough understanding of the invention and for purposes of explanation and not limitation, specific details are set forth, such as a particular geometry of the processing system and various descriptions of the system components. However, it should be understood that the invention may be practiced with other embodiments that depart from these specific details.

Figure 1:
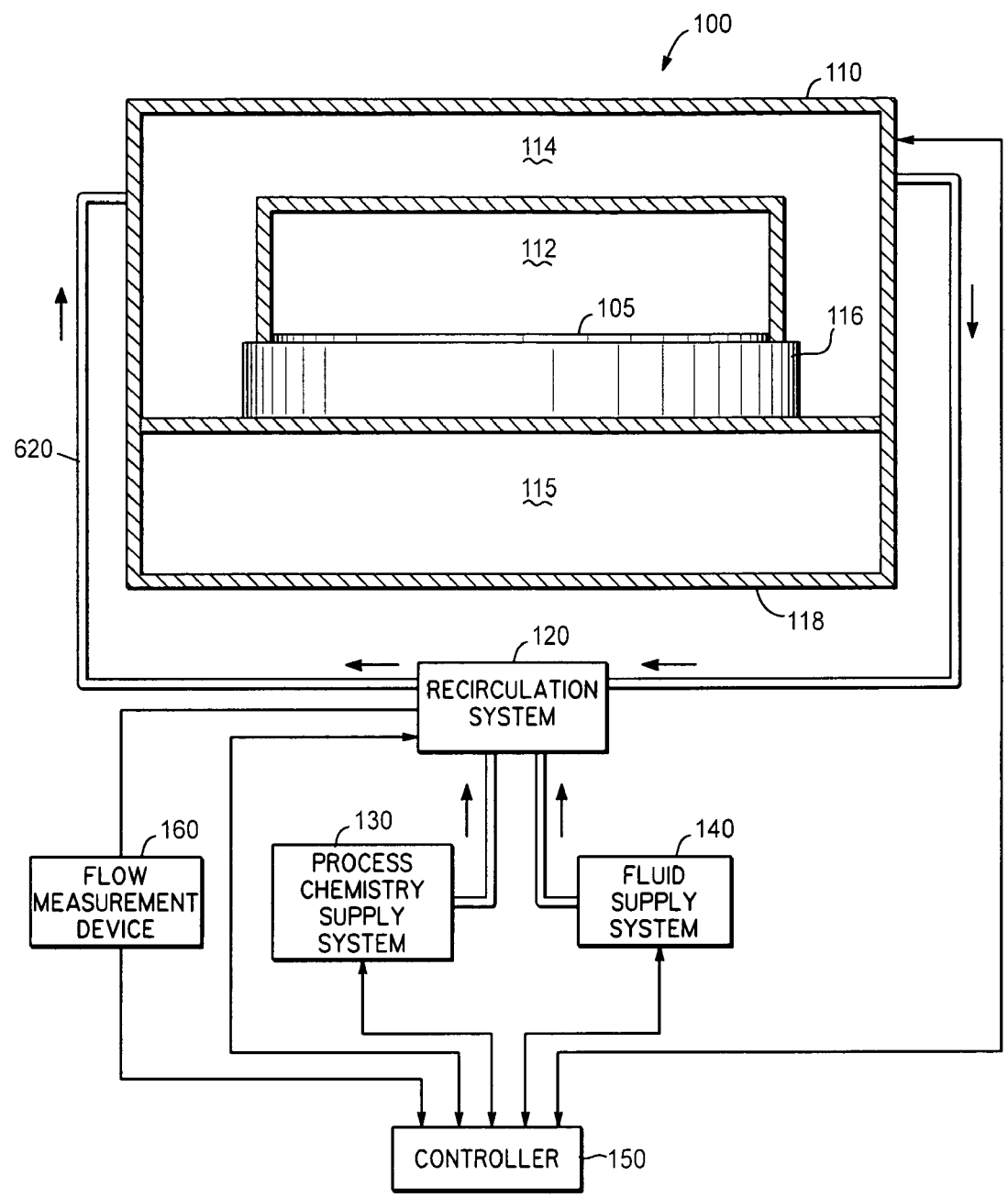
FIG. 1 presents a simplified schematic representation of a processing system.

Referring now to the drawings, wherein like reference numerals designate identical or corresponding parts throughout the several views, FIG. 1 illustrates a processing system 100 according to an embodiment of the invention. In the illustrated embodiment, processing system 100 is configured to treat a substrate 105 with a high pressure fluid, such as a fluid in a supercritical state, and an additive, such as a process chemistry. The processing system 100 comprises processing elements that include a processing chamber 110, a fluid flow system 120, a process chemistry supply system 130, a high pressure fluid supply system 140, a controller 150, and a flow measurement device 160, all of which are configured to process substrate 105. The controller 150 can be coupled to the processing chamber 110, the fluid flow system 120, the process chemistry supply system 130, the high pressure fluid supply system 140, and the flow measurement device 160.

Alternately, or in addition, controller 150 can be coupled to a one or more additional controllers/computers (not shown), and controller 150 can obtain setup and/or configuration information from an additional controller/computer.

In FIG. 1, singular processing elements (110, 120, 130, 140, 150, and 160) are shown, but this is not required for the invention. The processing system 100 can comprise any number of processing elements having any number of controllers associated with them in addition to independent processing elements.

The controller 150 can be used to configure any number of processing elements (110, 120, 130, 140, and 160), and the controller 150 can collect, provide, process, store, and display data from processing elements. The controller 150 can comprise a number of applications for controlling one or more of the processing elements. For example, controller 150 can include a graphic user interface (GUI) component (not shown) that can provide easy to use interfaces that enable a user to monitor and/or control one or more processing elements.

Referring still to FIG. 1, the fluid flow system 120 is configured to flow fluid and chemistry from the supplies 130 and 140 through the processing chamber 110. The fluid flow system 120 is illustrated as a recirculation system through which the fluid and chemistry recirculate from and back to the processing chamber 110 via primary flow line 620. This recirculation is most likely to be the preferred configuration for many applications, but this is not necessary to the invention. Fluids, particularly inexpensive fluids, can be passed through the processing chamber 110 once and then discarded, which might be more efficient than reconditioning them for re-entry into the processing chamber. Accordingly, while the fluid flow system or recirculation system 120 is described as a recirculating system in the exemplary embodiments, a non-recirculating system may, in some cases, be substituted. This fluid flow system 120 can include one or more valves (not shown) for regulating the flow of a processing solution through the fluid flow system 120 and through the processing chamber 110. The fluid flow system 120 can comprise any number of back-flow valves, filters, pumps, and/or heaters (not shown) for maintaining a specified temperature, pressure or both for the processing solution and for flowing the process solution through the fluid flow system 120 and through the processing chamber 110. Furthermore, any one of the many components provided within the fluid flow system 120 may be heated to a temperature consistent with the specified process temperature.

Some components, such as a fluid flow or recirculation pump, may require cooling in order to permit proper functioning. For example, some commercially available pumps, having specifications required for processing performance at high pressure and cleanliness during supercritical processing, comprise components that are limited in temperature. Therefore, as the temperature of the fluid and structure are elevated, cooling of the pump is required to maintain its functionality. Fluid flow system 120 for circulating the supercritical fluid through processing chamber 110 can comprise a primary flow line 620 coupled to high pressure processing system 100, and configured to supply the supercritical fluid at a fluid temperature equal to or greater than 40 degrees C. to the high pressure processing system 100, and a high temperature pump 600, shown and described below with reference to FIGS. 2A and 2B, coupled to the primary flow line 620. The high temperature pump 600 can be configured to move the supercritical fluid through the primary flow line 620 to the processing chamber 110, wherein the high temperature pump comprises a coolant inlet configured to receive a coolant and a coolant outlet configured to discharge the coolant. A heat exchanger coupled to the coolant inlet can be configured to lower a coolant temperature of the coolant to a temperature less than or equal to the fluid temperature of the supercritical fluid.

Figure 2A:
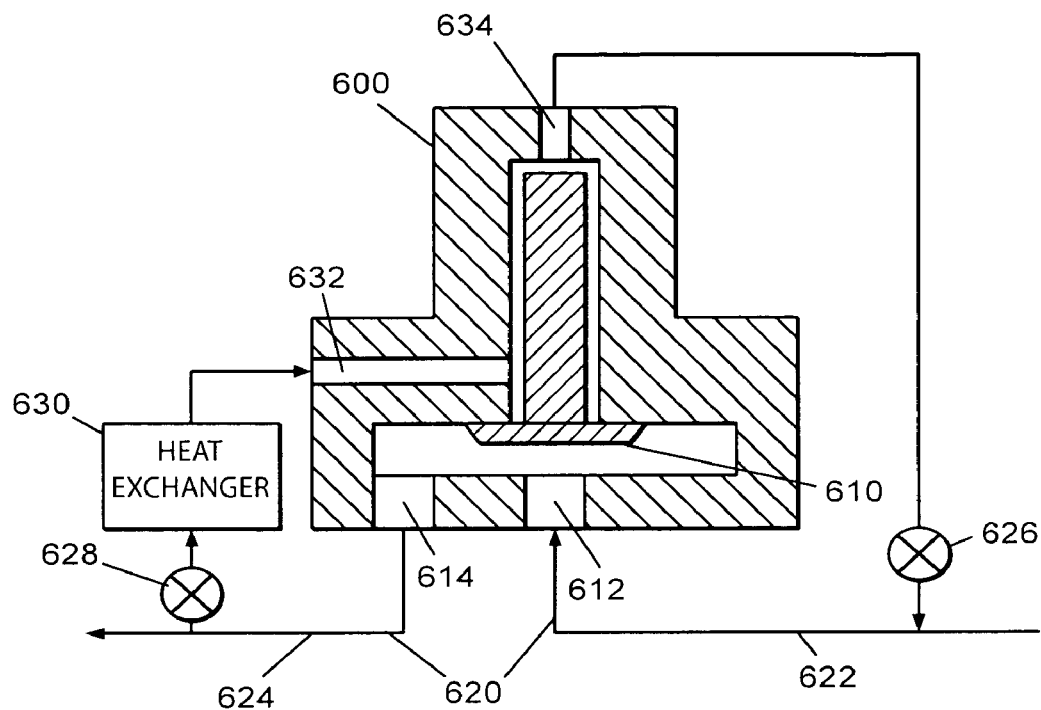
FIG. 2A depicts a system configured to cool a pump.

As illustrated in FIG. 2A, one embodiment is provided for cooling a high temperature pump 600 associated with fluid flow system 120 (or 220 described below with reference to FIG. 3) by diverting high pressure fluid from a primary flow line 620 to the high pressure processing chamber 110 (or 210) through a heat exchanger 630, through the pump 600, and back to the primary flow line 620. For example, a pump impeller 610 housed within pump 600 can move high pressure fluid from a suction side 622 of primary flow line 620 through an inlet 612 and through an outlet 614 to a pressure side 624 of the primary flow line 620. A fraction of high pressure fluid can be diverted through an inlet valve 628, through heat exchanger 630, and enter pump 600 through coolant inlet 632. Thereafter, the fraction of high pressure fluid utilized for cooling can exit from pump 600 at coolant outlet 634 and return to the primary flow line 620 through outlet valve 626.

Figure 2B:
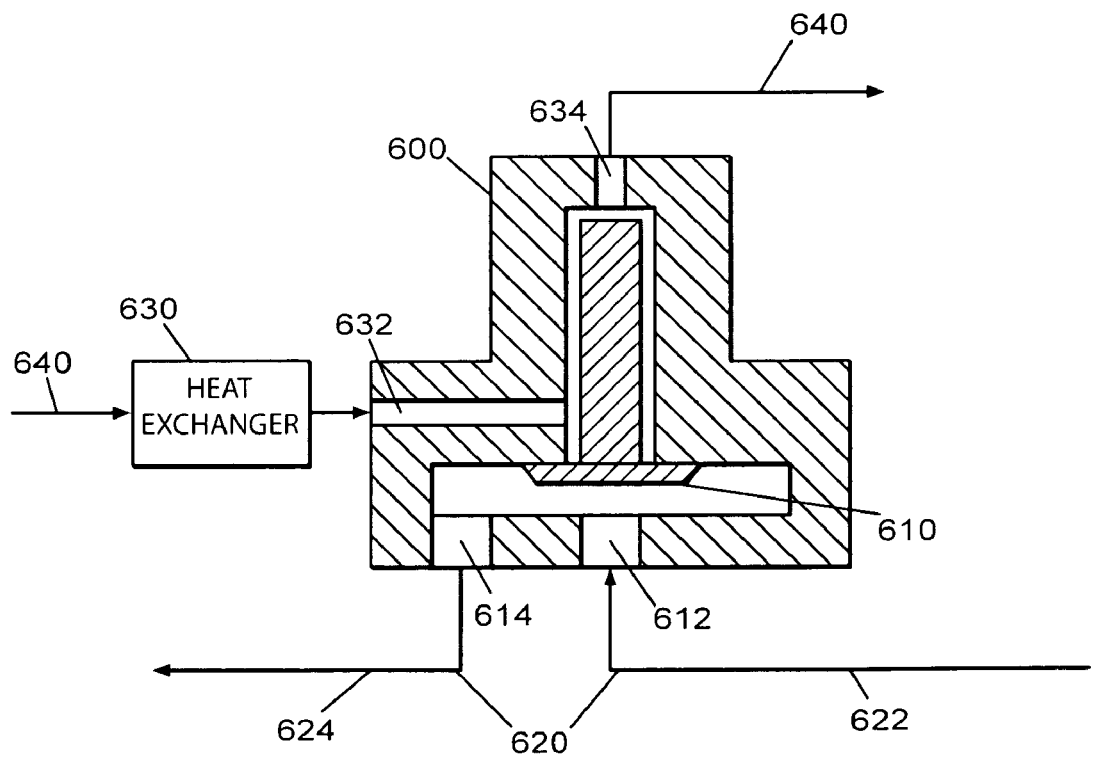
FIG. 2B depicts another system configured to cool a pump.

Alternatively, as illustrated in FIG. 2B, another embodiment is provided for cooling pump 600 using a secondary flow line 640. A high pressure fluid, such as a supercritical fluid, from a fluid source (not shown) is directed through heat exchanger 630 (to lower the temperature of the fluid), and then enters pump 600 through coolant inlet 632, passes through pump 600, exits through coolant outlet 634, and continues to a discharge system (not shown). The fluid source can include a supercritical fluid source, such as a supercritical carbon dioxide source. The fluid source may or may not be a member of the high pressure fluid supply system 140 (or 240) described in FIG. 1 (or FIG. 3). The discharge system can include a vent, or the discharge system can include a recirculation system having a pump configured to recirculate the high pressure fluid through the heat exchanger 630 and pump 600.

Additional details regarding pump design are provided in co-pending U.S. patent application Ser. No. 10/987,066, entitled "Method and System for Cooling a Pump"; the entire content of which is herein incorporated by reference in its entirety.

Referring again to FIG. 1, the processing system 100 can comprise high pressure fluid supply system 140. The high pressure fluid supply system 140 can be coupled to the fluid flow system 120, but this is not required. In alternate embodiments, high pressure fluid supply system 140 can be configured differently and coupled differently. For example, the fluid supply system 140 can be coupled directly to the processing chamber 110. The high pressure fluid supply system 140 can include a supercritical fluid supply system. A supercritical fluid as referred to herein is a fluid that is in a supercritical state, which is that state that exists when the fluid is maintained at or above the critical pressure and at or above the critical temperature on its phase diagram. In such a supercritical state, the fluid possesses certain properties, one of which is the substantial absence of surface tension. Accordingly, a supercritical fluid supply system, as referred to herein, is one that delivers to a processing chamber a fluid that assumes a supercritical state at the pressure and temperature at which the processing chamber is being controlled. Furthermore, it is only necessary that at least at or near the critical point the fluid is in substantially a supercritical state at which its properties are sufficient, and exist long enough, to realize their advantages in the process being performed. Carbon dioxide, for example, is a supercritical fluid when maintained at or above a pressure of about 1,070 psi at a temperature of 31 degrees C. This state of the fluid in the processing chamber may be maintained by operating the processing chamber at 2,000 to 10,000 psi at a temperature of approximately 40 degrees C. or greater.

As described above, the fluid supply system 140 can include a supercritical fluid supply system, which can be a carbon dioxide supply system. For example, the fluid supply system 140 can be configured to introduce a high pressure fluid having a pressure substantially near the critical pressure for the fluid. Additionally, the fluid supply system 140 can be configured to introduce a supercritical fluid, such as carbon dioxide in a supercritical state. Additionally, for example, the fluid supply system 140 can be configured to introduce a supercritical fluid, such as supercritical carbon dioxide, at a pressure ranging from approximately the critical pressure of carbon dioxide to 10,000 psi. Examples of other supercritical fluid species useful in the broad practice of the invention include, but are not limited to, carbon dioxide (as described above), oxygen, argon, krypton, xenon, ammonia, methane, methanol, dimethyl ketone, hydrogen, water, and sulfur hexafluoride. The fluid supply system can, for example, comprise a carbon dioxide source (not shown) and a plurality of flow control elements (not shown) for generating a supercritical fluid. For example, the carbon dioxide source can include a $CO_2$ feed system, and the flow control elements can include supply lines, valves, filters, pumps, and heaters. The fluid supply system 140 can comprise an inlet valve (not shown) that is configured to open and close to allow or prevent the stream of supercritical carbon dioxide from flowing into the processing chamber 110. For example, controller 150 can be used to determine fluid parameters such as pressure, temperature, process time, and flow rate.

Referring still to FIG. 1, the process chemistry supply system 130 is coupled to the recirculation system 120, but this is not required for the invention. In alternate embodiments, the process chemistry supply system 130 can be configured differently, and can be coupled to different elements in the processing system 100. The process chemistry is introduced by the process chemistry supply system 130 into the fluid introduced by the fluid supply system 140 at ratios that vary with the substrate properties, the chemistry being used and the process being performed in the processing chamber 110. Usually the ratio is roughly 1 to 15 percent by volume, which, for a chamber, recirculation system and associated plumbing having a volume of about one liter amounts to about 10 to 150 milliliters of additive in most cases, but the ratio may be higher or lower.

The process chemistry supply system 130 can be configured to introduce one or more of the following process compositions, but not limited to: cleaning compositions for removing contaminants, residues, hardened residues, photoresist, hardened photoresist, post-etch residue, post-ash residue, post chemical-mechanical polishing (CMP) residue, post-polishing residue, or post-implant residue, or any combination thereof; cleaning compositions for removing particulate; drying compositions for drying thin films, porous thin films, porous low dielectric constant materials, or air-gap dielectrics, or any combination thereof; film-forming compositions for preparing dielectric thin films, metal thin films, or any combination thereof; healing compositions for restoring the dielectric constant of low dielectric constant (low-k) films; sealing compositions for sealing porous films; or any combination thereof. Additionally, the process chemistry supply system 130 can be configured to introduce solvents, co-solvents, surfactants, etchants, acids, bases, chelators, oxidizers, film-forming precursors, or reducing agents, or any combination thereof.

The process chemistry supply system 130 can be configured to introduce N-methylpyrrolidone (NMP), diglycol amine, hydroxylamine, di-isopropyl amine, tri-isoprpyl amine, tertiary amines, catechol, ammonium fluoride, ammonium bifluoride, methylacetoacetamide, ozone, propylene glycol monoethyl ether acetate, acetylacetone, dibasic esters, ethyl lactate, $CHF_3$, $BF_3$, HF, other fluorine containing chemicals, or any mixture thereof. Other chemicals such as organic solvents may be utilized independently or in conjunction with the above chemicals to remove organic materials. The organic solvents may include, for example, an alcohol, ether, and/or glycol, such as acetone, diacetone alcohol, dimethyl sulfoxide (DMSO), ethylene glycol, methanol, ethanol, propanol, or isopropanol (IPA). For further details, see U.S. Pat. No. 6,306,564, filed May 27, 1998, and titled "REMOVAL OF RESIST OR RESIDUE FROM SEMICONDUCTORS USING SUPERCRITICAL CARBON DIOXIDE", and U.S. Pat. No. 6,509,141, filed Sep. 3, 1999, and titled "REMOVAL OF PHOTORESIST AND PHOTORESIST RESIDUE FROM SEMICONDUCTORS USING SUPERCRITICAL CARBON DIOXIDE PROCESS," both incorporated by reference herein.

Additionally, the process chemistry supply system 130 can comprise a cleaning chemistry assembly (not shown) for providing cleaning chemistry for generating supercritical cleaning solutions within the processing chamber. The cleaning chemistry can include peroxides and a fluoride source. For example, the peroxides can include hydrogen peroxide, benzoyl peroxide, or any other suitable peroxide, and the fluoride sources can include fluoride salts (such as ammonium fluoride salts), hydrogen fluoride, fluoride adducts (such as organo-ammonium fluoride adducts), and combinations thereof. Further details of fluoride sources and methods of generating supercritical processing solutions with fluoride sources are described in U.S. patent application Ser. No. 10/442,557, filed May 20, 2003, and titled "TETRA-ORGANIC AMMONIUM FLUORIDE AND HF IN SUPERCRITICAL FLUID FOR PHOTORESIST AND RESIDUE REMOVAL", and U.S. patent application Ser. No. 10/321,341, filed Dec. 16, 2002, and titled "FLUORIDE IN SUPERCRITICAL FLUID FOR PHOTORESIST POLYMER AND RESIDUE REMOVAL," both incorporated by reference herein.

Furthermore, the process chemistry supply system 130 can be configured to introduce chelating agents, complexing agents and other oxidants, organic and inorganic acids that can be introduced into the supercritical fluid solution with one or more carrier solvents, such as N,N-dimethylacetamide (DMAc), gamma-butyrolactone (BLO), dimethyl sulfoxide (DMSO), ethylene carbonate (EC), butylenes carbonate (BC), propylene carbonate (PC), N-methylpyrrolidone (NMP), dimethylpiperidone, propylene carbonate, and alcohols (such a methanol, ethanol and 2-propanol).

Moreover, the process chemistry supply system 130 can comprise a rinsing chemistry assembly (not shown) for providing rinsing chemistry for generating supercritical rinsing solutions within the processing chamber. The rinsing chemistry can include one or more organic solvents including, but not limited to, alcohols and ketone. In one embodiment, the rinsing chemistry can comprise sulfolane, also known as thiocyclopentane-1,1-dioxide, (cyclo)tetramethylene sulphone and 2,3,4,5-tetrahydrothiophene-1,1-dioxide, which can be purchased from a number of venders, such as Degussa Stanlow Limited, Lake Court, Hursley Winchester SO21 2LD UK.

Moreover, the process chemistry supply system 130 can be configured to introduce treating chemistry for curing, cleaning, healing (or restoring the dielectric constant of low-k materials), or sealing, or any combination thereof, low dielectric constant films (porous or non-porous). The chemistry can include hexamethyldisilazane (HMDS), chlorotrimethylsilane (TMCS), trichloromethylsilane (TCMS), dimethylsilyldiethylamine (DMSDEA), tetramethyldisilazane (TMDS), trimethylsilyldimethylamine (TMSDMA), dimethylsilyldimethylamine (DMSDMA), trimethylsilyldiethylamine (TMSDEA), bistrimethylsilyl urea (BTSU), bis(dimethylamino)methyl silane (B[DMA]MS), bis(dimethylamino)dimethyl silane (B[DMA]DS), HMCTS, dimethylaminopentamethyldisilane (DMAPMDS), dimethylaminodimethyldisilane (DMADMDS), disila-aza-cyclopentane (TDACP), disila-oza-cyclopentane (TDOCP), methyltrimethoxysilane (MTMOS), vinyltrimethoxysilane (VTMOS), or trimethylsilylimidazole (TMSI). Additionally, the chemistry may include N-tert-butyl-1,1-dimethyl-1-(2,3,4,5-tetramethyl-2,4-cyclopentadiene-1-yl)silanamine, 1,3-diphenyl-1,1,3,3-tetramethyldisilazane, or tert-butylchlorodiphenylsilane. For further details, see U.S. patent application Ser. No. 10/682,196, filed Oct. 10, 2003, and titled "METHOD AND SYSTEM FOR TREATING A DIELECTRIC FILM," and U.S. patent application Ser. No. 10/379,984, filed Mar. 4, 2003, and titled "METHOD OF PASSIVATING LOW DIELECTRIC MATERIALS IN WAFER PROCESSING," both incorporated by reference herein.

Moreover, the process chemistry supply system 130 can be configured to introduce a peroxide during, for instance, cleaning processes. The peroxide can be introduced with any one of the above process chemistries, or any mixture thereof. The peroxide can include organic peroxides, or inorganic peroxides, or a combination thereof. For example, organic peroxides can include 2-butanone peroxide; 2,4-pentanedione peroxide; peracetic acid; t-butyl hydroperoxide; benzoyl peroxide; or m-chloroperbenzoic acid (mCPBA). Other peroxides can include hydrogen peroxide. Alternatively, the peroxide can include a diacyl peroxide, such as: decanoyl peroxide; lauroyl peroxide; succinic acid peroxide; or benzoyl peroxide; or any combination thereof. Alternatively, the peroxide can include a dialkyl peroxide, such as: dicumyl peroxide; 2,5-di(t-butylperoxy)-2,5-dimethylhexane; t-butyl cumyl peroxide; α,α-bis(t-butylperoxy)diisopropylbenzene mixture of isomers; di(t-amyl) peroxide; di(t-butyl) peroxide; or 2,5-di(t-butylperoxy)-2,5-dimethyl-3-hexyne; or any combination thereof. Alternatively, the peroxide can include a diperoxyketal, such as: 1,1-di(t-butylperoxy)-3,3,5-trimethylcyclohexane; 1,1-di(t-butylperoxy)cyclohexane; 1,1-di(t-amylperoxy)-cyclohexane; n-butyl 4,4-di(t-butylperoxy)valerate; ethyl 3,3-di-(t-amylperoxy)butanoate; t-butyl peroxy-2-ethylhexanoate; or ethyl 3,3-di(t-butylperoxy)butyrate; or any combination thereof. Alternatively, the peroxide can include a hydroperoxide, such as: cumene hydroperoxide; or t-butyl hydroperoxide; or any combination thereof. Alternatively, the peroxide can include a ketone peroxide, such as: methyl ethyl ketone peroxide; or 2,4-pentanedione peroxide; or any combination thereof. Alternatively, the peroxide can include a peroxydicarbonate, such as: di(n-propyl)peroxydicarbonate; di(sec-butyl)peroxydicarbonate; or di(2-ethylhexyl)peroxydicarbonate; or any combination thereof. Alternatively, the peroxide can include a peroxyester, such as: 3-hydroxyl-1,1-dimethylbutyl peroxyneodecanoate; α-cumyl peroxyneodecanoate; t-amyl peroxyneodecanoate; t-butyl peroxyneodecanoate; t-butyl peroxypivalate; 2,5-di(2-ethylhexanoylperoxy)-2,5-dimethylhexane; t-amyl peroxy-2-ethylhexanoate; t-butyl peroxy-2-ethylhexanoate; t-amyl peroxyacetate; t-butyl peroxyacetate; t-butyl peroxybenzoate; OO-(t-amyl)O-(2-ethylhexyl)monoperoxycarbonate; OO-(t-butyl)O-isopropyl monoperoxycarbonate; OO-(t-butyl)O-(2-ethylhexyl) monoperoxycarbonate; polyether poly-t-butylperoxy carbonate; or t-butyl peroxy-3,5,5-trimethylhexanoate; or any combination thereof. Alternatively, the peroxide can include any combination of peroxides listed above.

Moreover, the process chemistry supply system 130 can be configured to introduce fluorosilicic acid. Alternatively, the process chemistry supply system is configured to introduce fluorosilicic acid with a solvent, a co-solvent, a surfactant, an acid, a base, a peroxide, or an etchant. Alternatively, the fluorosilicic acid can be introduced in combination with any of the chemicals presented above. For example, fluorosilicic acid can be introduced with N,N-dimethylacetamide (DMAc), gamma-butyrolactone (BLO), dimethyl sulfoxide (DMSO), ethylene carbonate (EC), butylene carbonate (BC), propylene carbonate (PC), N-methylpyrrolidone (NMP), dimethylpiperidone, propylene carbonate, or an alcohol (such a methanol (MeOH), isopropyl alcohol (IPA), and ethanol).

The processing chamber 110 can be configured to process substrate 105 by exposing the substrate 105 to fluid from the fluid supply system 140, or process chemistry from the process chemistry supply system 130, or a combination thereof in a processing space 112. Additionally, processing chamber 110 can include an upper chamber assembly 114, and a lower chamber assembly 115.

The upper chamber assembly 114 can comprise a heater (not shown) for heating the processing chamber 110, the substrate 105, or the processing fluid, or a combination of two or more thereof. Alternately, a heater is not required. Additionally, the upper chamber assembly 114 can include flow components for flowing a processing fluid through the processing chamber 110. In one example, a circular flow pattern can be established. Alternately, the flow components for flowing the fluid can be configured differently to affect a different flow pattern. Alternatively, the upper chamber assembly 114 can be configured to fill the processing chamber 110.

The lower chamber assembly 115 can include a platen 116 configured to support substrate 105 and a drive mechanism 118 for translating the platen 116 in order to load and unload substrate 105, and seal lower chamber assembly 115 with upper chamber assembly 114. The platen 116 can also be configured to heat or cool the substrate 105 before, during, and/or after processing the substrate 105. For example, the platen 116 can include one or more heater rods configured to elevate the temperature of the platen to approximately 31 degrees C. or greater. Additionally, the lower assembly 115 can include a lift pin assembly for displacing the substrate 105 from the upper surface of the platen 116 during substrate loading and unloading.

Referring still to FIG. 1, processing system 100 further comprises flow measurement device 160 coupled to fluid flow system 120. The flow measurement device 160 is configured to measure a flow parameter related to the flow of high pressure fluid and process chemistry through processing chamber 110. The inventor has observed that maintaining a constant flow rate from one substrate to the next substrate contributes to the repeatability of process results, such as cleaning results. For example, the flow parameter can include a flow rate, such as a velocity, a mass flow rate, a volume flow rate, etc.

Measuring, monitoring or otherwise determining flow parameters is useful for controlling or otherwise maintaining desirable flow parameters, for example maintaining constant a flow rate or another parameter, from wafer to wafer. Alternatively, the measurement or other determination can be used to compensate for variations in flow conditions, such as by making compensating changes to another process. Action taken in response to the flow condition determination can be carried out by operator response or automatically. In the illustrated embodiment of FIG. 1, for example, the output of the flow measurement device is communicated to the controller 150, which in response, can control the chamber 110, the fluid flow system 120, the process chemistry supply system 130, the fluid supply system 140, or some other component or system.

In one embodiment, the flow measurement device 160 comprises a coriolis meter, such as a micro-motion coriolis meter, model no. DH038S999SU, commercially available from Emerson Process Management. In another embodiment, the flow measurement device 160 comprises a turbidity meter, such as model no. FS-V21RM, commercially available from the Keyence Corporation. The turbidity meter employs an optical technique, including an optical source and an optical sensor, whereby changes in the intensity of back-scattered light or changes in the intensity of forward-scattered light represent changes in the composition of the fluid medium passing the optical volume residing between the optical source and the optical sensor.

For instance, upon injecting the process chemistry into the high pressure fluid flowing through fluid flow system 120, the local concentration of process chemistry is high until, in time, the process chemistry disperses throughout the high pressure fluid and, if soluble, dissolves within the high pressure fluid. In one example, the fluid flow system 120 includes a recirculation system as described above and shown in FIG. 1. In such a system, the process chemistry circulates through the fluid flow system 120 a number of times until it is fully mixed with the high pressure fluid. When coupling a turbidity meter to the fluid flow system 120, a signal related to the local concentration of process chemistry can be obtained. This signal exhibits signal variations when the undissolved process chemistry passes the turbidity meter.

Figure 3:
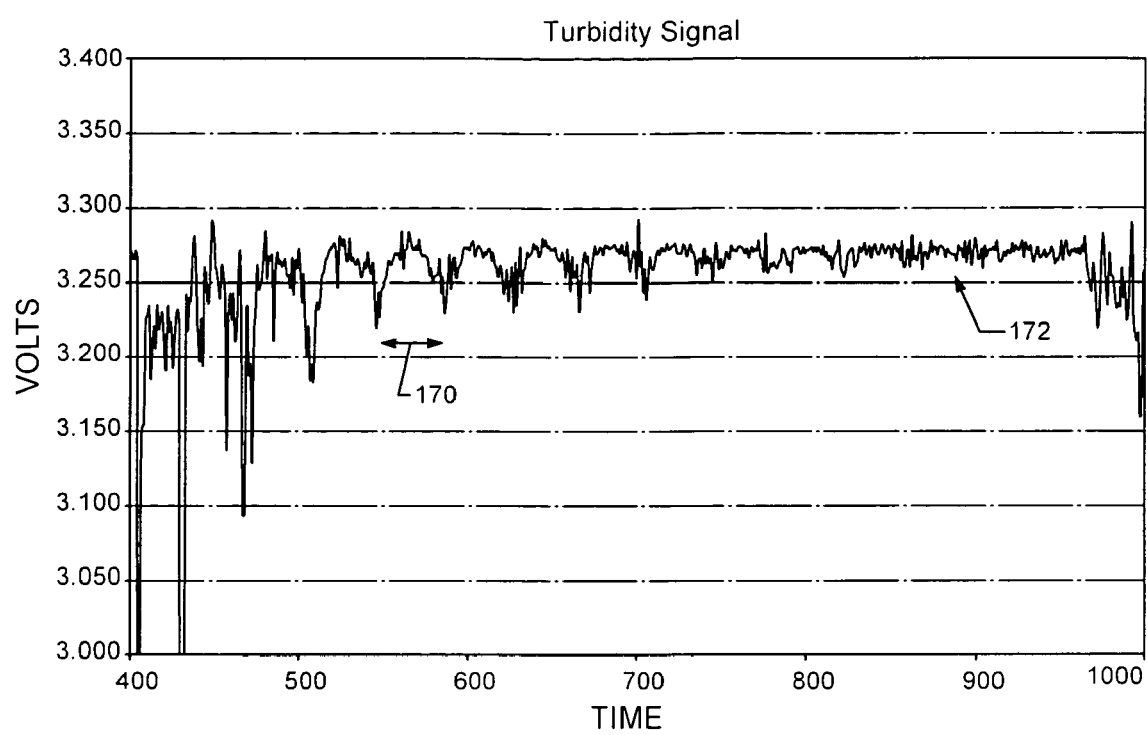
FIG. 3 is a graph illustrating the determination of a flow parameter in a processing system according to an embodiment of the invention.

Referring now to FIG. 3, a signal, in volts, output from the turbidity meter is plotted versus time. The signal is a result of injecting a small amount of soluble process chemistry into a flowing high pressure fluid, and, in this particular case, 30 milliliters (ml) of methanol (MeOH) is added to 1300 ml of supercritical carbon dioxide. Moreover, the signal exhibits a periodic variation in voltage, separated in time by a time period (Dt) 170 characteristic of the time required for the undissolved process chemistry to circulate from a point in the system at which the measurement is taken, through the fluid flow system 120, and back to the point of measurement. A volume flow rate can be determined by measuring the time period 170 from peak-to-peak of variations in the signal, and dividing the known volume of fluid by the measured time period 170. The time period 170 can, for example, be determined using Fourier analysis and converting the time signal into frequency space. Additionally, a mixing time 172 for introducing the process chemistry into the high pressure fluid can be determined by observing when the disturbances in voltage subside to a negligible amount. Once a flow rate is measured, the measured flow rate may be compared with a target flow rate, and a difference may be utilized to adjust the flow rate to the target flow rate.

In another embodiment, two or more turbidity meters may be used, whereby the known distance between the meters in the fluid flow system 120, and a time difference between a first time associated with the passing of a flow disturbance, such as injected process chemistry, by a first turbidity meter and a second time associated with the passing of the flow disturbance by a second turbidity meter can be utilized to determine a flow parameter, such as flow velocity.

An example of the use of the measurement of the flow rate with a turbidity meter, or with any other device, can be to compare the measurement at the controller 150 with a flow rate setting that is to be maintained. If the measured flow rate differs from the desired flow rate, for example if it is less due to build up of particles in a recirculation system filter, the controller 150 can control pumps, valves or other components of the fluid flow system 120 increase the flow rate to the desired condition.

In another embodiment of the invention, the flow condition determination can be a measurement of the homogeneity of the process chemistry in the high pressure fluid. For example, the output of the turbidity meter illustrated in FIG. 3 indicates the concentration of process chemistry in the fluid as a function of time in the fluid passing the flow measurement device 160. Where the period 170 reflects the time period for fluid to cycle through the recirculation system 120, the amplitude variation of the meter output during a given cycle reflects the degree of inhomogeneity of the chemistry in the fluid.

In a typical supercritical fluid cleaning process, after a wafer to be cleaned is placed in the chamber 110, fluid is circulated through the system, often through a chamber bypass loop, and then chemistry is injected. Several cycles 170 are required before the concentration of the chemistry is sufficiently uniform to begin the wafer cleaning process. From that point, a minimum cleaning time is needed for any given wafer. To avoid premature commencement of the cleaning, a typical system must allow a sufficiently long time delay to allow for the worst case so as to insure that the fluid and process chemistry are sufficiently mixed. This delay adds to the process time and reduces machine throughput, and thus productivity.

In accordance with an embodiment of the invention, arrival at the desired uniformity can be detected by sensing with the flow measurement device 160 when the fluctuations in the output of the turbidity meter are small enough to indicate adequate fluid homogeneity. At this point in time, the cleaning of the wafer presently in the chamber 110 can start. This minimizes the delay of the cleaning of each wafer to the minimum needed to arrive at fluid homogeneity, thereby optimizing process time and throughput compared with the use of a single startup delay that is long enough to provide for the worst case.

Additionally, controller 150 includes a temperature control system coupled to one or more of the processing chamber 110, the fluid flow system 120 (or recirculation system), the platen 116, the high pressure fluid supply system 140, or the process chemistry supply system 130. The temperature control system is coupled to heating elements embedded in one or more of these systems, and configured to elevate the temperature of the supercritical fluid to approximately 31 degrees C. or greater. The heating elements can, for example, include resistive heating elements.

A transfer system (not shown) can be used to move a substrate into and out of the processing chamber 110 through a slot (not shown). In one example, the slot can be opened and closed by moving the platen 116, and in another example, the slot can be controlled using a gate valve (not shown).

The substrate can include semiconductor material, metallic material, dielectric material, ceramic material, or polymer material, or a combination of two or more thereof. The semiconductor material can include Si, Ge, Si/Ge, or GaAs. The metallic material can include Cu, Al, Ni, Pb, Ti, and/or Ta. The dielectric material can include silica, silicon dioxide, quartz, aluminum oxide, sapphire, low dielectric constant materials, TEFLON®, and/or polyimide. The ceramic material can include aluminum oxide, silicon carbide, etc.

The processing system 100 can also comprise a pressure control system (not shown). The pressure control system can be coupled to the processing chamber 110, but this is not required. In alternate embodiments, the pressure control system can be configured differently and coupled differently. The pressure control system can include one or more pressure valves (not shown) for exhausting the processing chamber 110 and/or for regulating the pressure within the processing chamber 110. Alternately, the pressure control system can also include one or more pumps (not shown). For example, one pump may be used to increase the pressure within the processing chamber, and another pump may be used to evacuate the processing chamber 110. In another embodiment, the pressure control system can comprise seals for sealing the processing chamber. In addition, the pressure control system can comprise an elevator for raising and lowering the substrate 105 and/or the platen 116.

Furthermore, the processing system 100 can comprise an exhaust control system. The exhaust control system can be coupled to the processing chamber 110, but this is not required. In alternate embodiments, the exhaust control system can be configured differently and coupled differently. The exhaust control system can include an exhaust gas collection vessel (not shown) and can be used to remove contaminants from the processing fluid. Alternately, the exhaust control system can be used to recycle the processing fluid.

Figure 4:
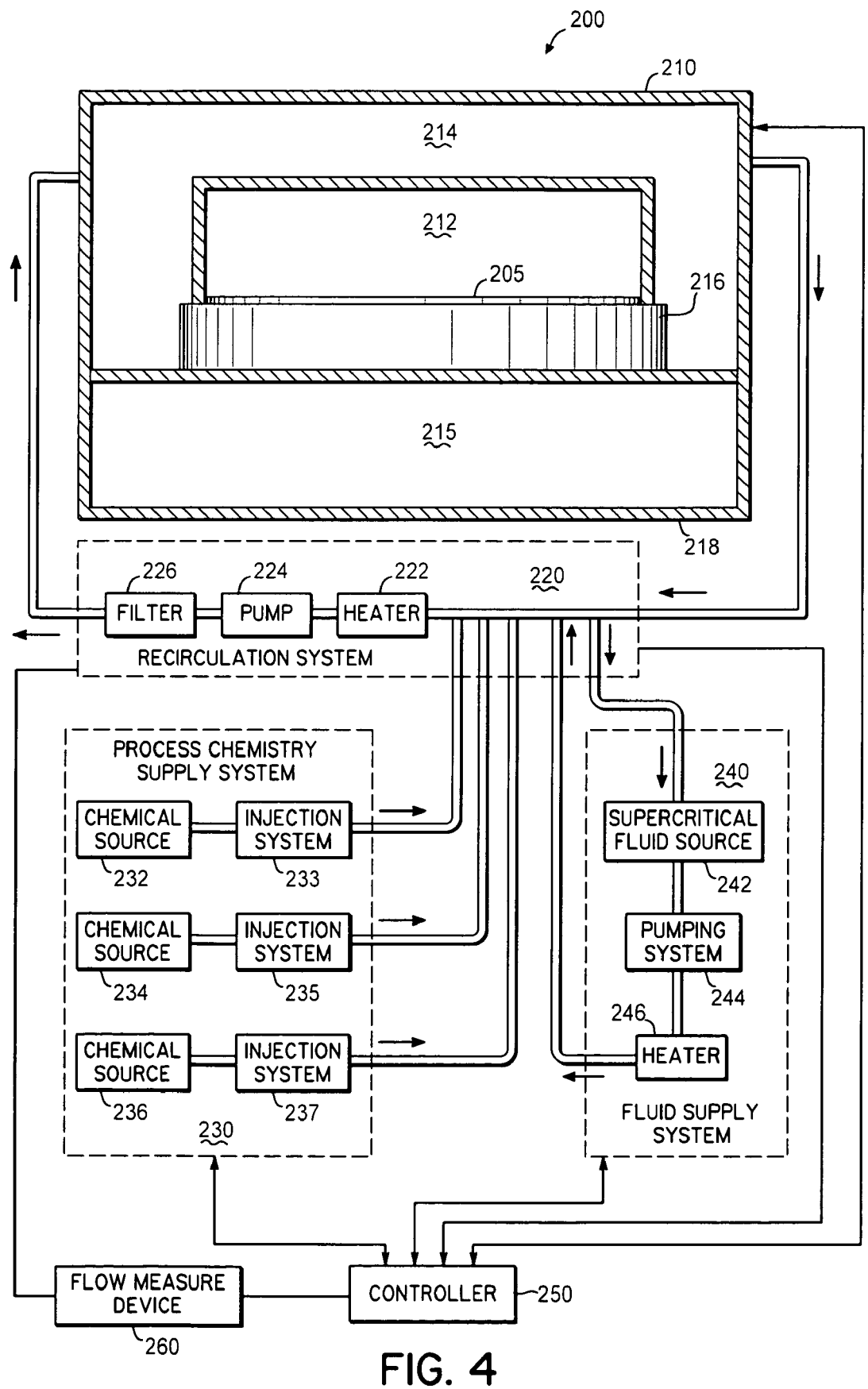
FIG. 4 presents another simplified schematic representation of a processing system.

Referring now to FIG. 4, a processing system 200 is presented according to another embodiment. In the illustrated embodiment, processing system 200 comprises a processing chamber 210, a recirculation system 220, a process chemistry supply system 230, a fluid supply system 240, a controller 250, and a flow measurement device 260, all of which are configured to process substrate 205. The controller 250 can be coupled to the processing chamber 210, the recirculation system 220, the process chemistry supply system 230, the fluid supply system 240, and the flow measurement device 260. Alternately, controller 250 can be coupled to one or more additional controllers/computers (not shown), and controller 250 can obtain setup and/or configuration information from an additional controller/computer.

As shown in FIG. 4, the recirculation system 220 can include a recirculation fluid heater 222, a pump 224, and a filter 226. The process chemistry supply system 230 can include one or more chemistry introduction systems, each introduction system having a chemical source 232, 234, 236, and an injection system 233, 235, 237. The injection systems 233, 235, 237 can include a pump (not shown) and an injection valve (not shown). For example, the chemical source can include a source of process chemistry, as described above. The process chemistry can be introduced in such a way that a flow parameter can be determined using the flow measurement device 260.

Furthermore, the fluid supply system 240 can include a supercritical fluid source 242, a pumping system 244, and a supercritical fluid heater 246. In addition, one or more injection valves, and/or exhaust valves may be utilized with the fluid supply system 240.

The processing chamber 210 can be configured to process substrate 205 by exposing the substrate 205 to fluid from the fluid supply system 240, or process chemistry from the process chemistry supply system 230, or a combination thereof in a processing space 212. Additionally, processing chamber 210 can include an upper chamber assembly 214, and a lower chamber assembly 215 having a platen 216 and drive mechanism 218, as described above with reference to FIG. 1.

Figure 5:
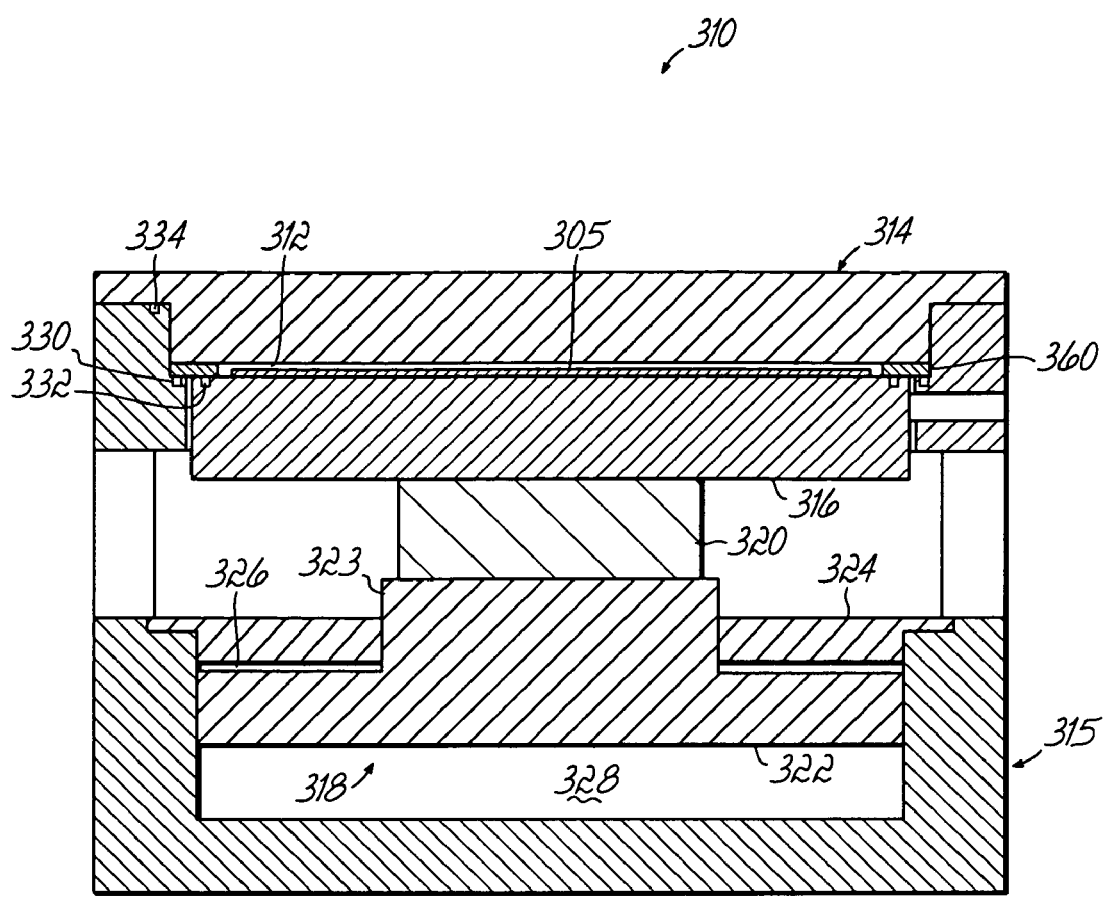
FIG. 5 presents another simplified schematic representation of a processing system.

Alternatively, the processing chamber 210 can be configured as described in pending U.S. patent application Ser. No. 09/912,844 (US Patent Application Publication No. 2002/0046707), entitled "High pressure processing chamber for semiconductor substrates", and filed on Jul. 24, 2001, which is incorporated herein by reference in its entirety. For example, FIG. 5 depicts a cross-sectional view of a supercritical processing chamber 310 comprising upper chamber assembly 314, lower chamber assembly 315, platen 316 configured to support substrate 305, and drive mechanism 318 configured to raise and lower platen 316 between a substrate loading/unloading condition and a substrate processing condition. Drive mechanism 318 can further include a drive cylinder 320, drive piston 322 having piston neck 323, sealing plate 324, pneumatic cavity 326, and hydraulic cavity 328. Additionally, supercritical processing chamber 310 further includes a plurality of sealing devices 330, 332, and 334 for providing a sealed, high pressure process space 312 in the processing chamber 310.

Figure 6A:
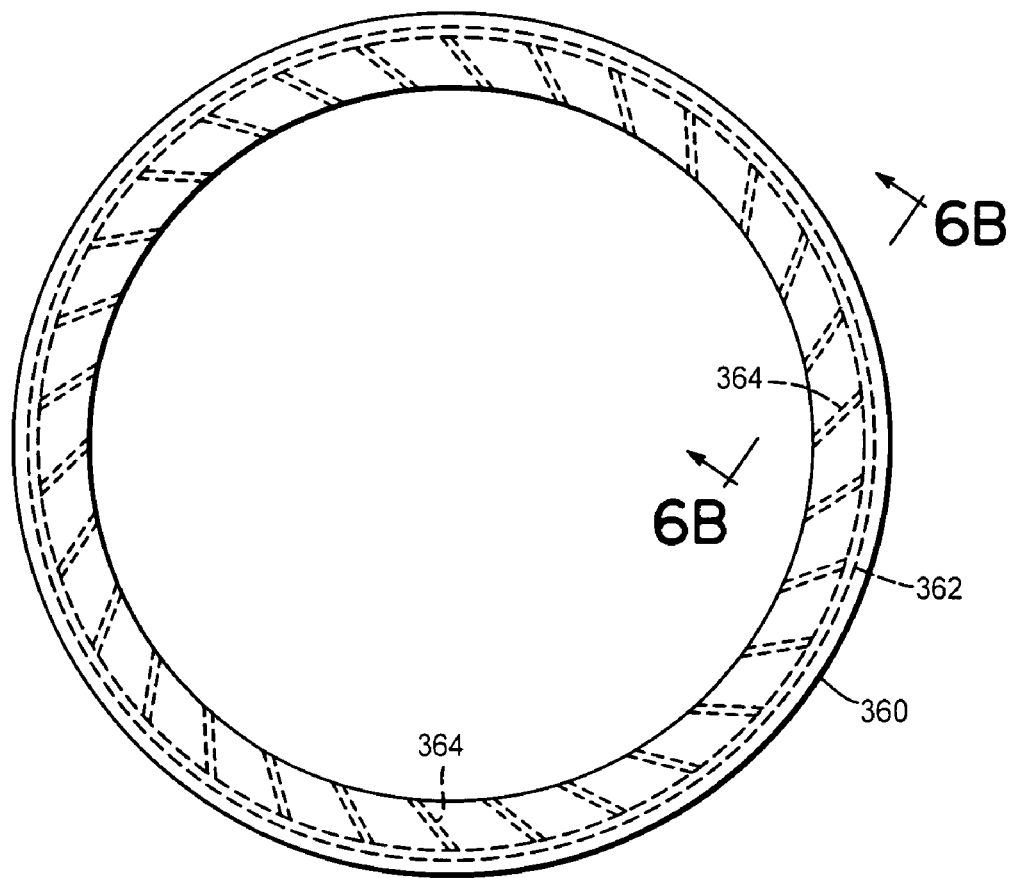
FIGS. 6A and 6B depict a fluid injection manifold for introducing fluid to a processing system.
Figure 6B:
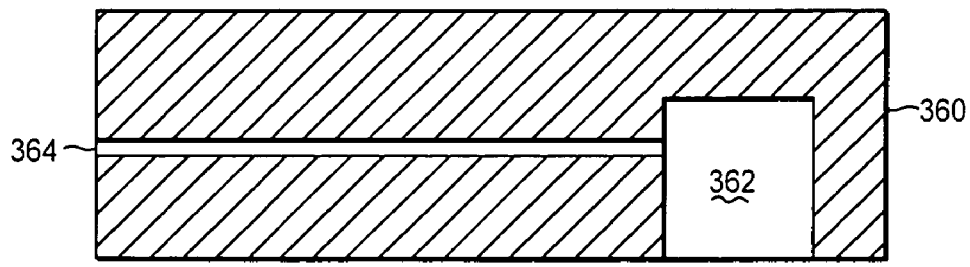

As described above with reference to FIGS. 1 and 4, the fluid flow or recirculation system coupled to the processing chamber is configured to circulate the fluid through the processing chamber, and thereby permit the exposure of the substrate in the processing chamber to a flow of fluid. The fluid, such as supercritical carbon dioxide with or without process chemistry, can enter the processing chamber at a peripheral edge of the substrate through one or more inlets coupled to the fluid flow system. For example, referring now to FIG. 5 and FIGS. 6A and 6B, an injection manifold 360 is shown as a ring having an annular fluid supply channel 362 coupled to one or more inlets 364. The one or more inlets 364, as illustrated, include forty five (45) injection orifices canted at 45 degrees, thereby imparting azimuthal momentum, or axial momentum, or both, as well as radial momentum to the flow of high pressure fluid through process space 312 above substrate 305. Although shown to be canted at an angle of 45 degrees, the angle may be varied, including direct radial inward injection.

Additionally, the fluid, such as supercritical carbon dioxide, exits the processing chamber adjacent a surface of the substrate through one or more outlets (not shown). For example, as described in U.S. patent application Ser. No. 09/912,844, the one or more outlets can include two outlet holes positioned proximate to and above the center of substrate 305. The flow through the two outlets can be alternated from one outlet to the next outlet using a shutter valve.

Alternatively, the fluid, such as supercritical carbon dioxide, can enter and exit from the processing chamber as described in pending U.S. patent application Ser. No. 11/018,922, entitled "Method and System for Flowing a Supercritical Fluid in a High Pressure Processing System"; the entire content of which is herein incorporated by reference in its entirety.

Figure 7:
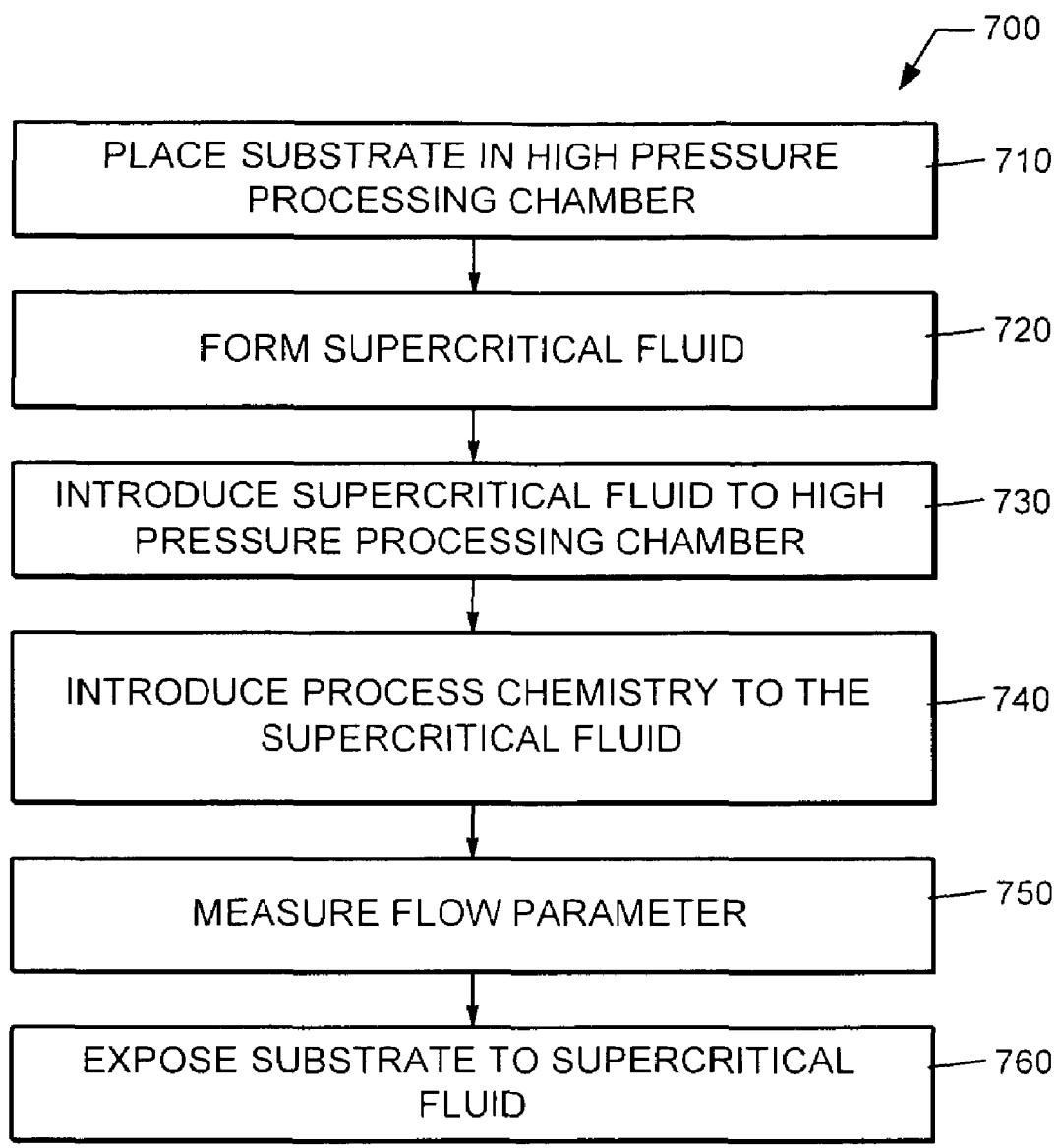
FIG. 7 illustrates a method of treating a substrate in a processing system according to an embodiment of the invention.

Referring now to FIG. 7, a method of treating a substrate with a fluid in a supercritical state is provided. As depicted in flow chart 700, the method begins in 710 with placing a substrate onto a platen within a high pressure processing chamber configured to expose the substrate to a supercritical fluid processing solution.

In 720, a supercritical fluid is formed by bringing a fluid in a subcritical state to a supercritical state by adjusting the pressure of the fluid to at or above the critical pressure of the fluid, and adjusting the temperature of the fluid to at or above the critical temperature of the fluid. In 730, the supercritical fluid is introduced to the high pressure processing chamber through one or more inlets and discharged through one or more outlets. Furthermore, the temperature of the supercritical fluid is further optionally elevated to a value equal to or greater than 40 degrees C. For example, the temperature of the supercritical fluid is set to equal or greater than 80 degrees C. By way of further example, the temperature of the supercritical fluid is set to equal or greater than 120 degrees C.

In 740, a process chemistry comprising is introduced to the supercritical fluid. For example, the process chemistry can include any combination of chemicals presented above. In 750, a flow parameter is measured using a flow measurement device coupled to the processing system. The flow measurement device can, for example, comprise a coriolis meter or a turbidity meter. Additionally, the measured flow parameter can be compared to a target flow parameter, and the flow rate of high pressure fluid can be adjusted according to the respective difference. For instance, when the measured flow rate exceeds the target flow rate, then the speed of a pump utilized to circulate high pressure fluid through the processing system can be decreased. Alternatively, when the target flow rate exceeds the measured flow rate, then the speed of a pump utilized to circulate high pressure fluid through the processing system can be increased. In 760, the substrate is exposed to the supercritical fluid.

In the embodiments described above, the flow measurement device and the method for measuring a flow parameter in a fluid flow system are provided for a high pressure fluid and, in particular, a supercritical fluid. However, the measurement device and technique should not be limited to high pressure fluid, but may also be applicable to any fluid flow.

Although only certain exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A method of treating a substrate comprising:
   placing said substrate in a high pressure processing chamber of a high pressure processing system onto a platen configured to support said substrate;
   forming a supercritical fluid from a fluid by adjusting a pressure of said fluid above the critical pressure of said fluid, and adjusting a temperature of said fluid above the critical temperature of said fluid;
   introducing said supercritical fluid to said high pressure processing chamber;
   introducing a process chemistry to said supercritical fluid;
   flowing said supercritical fluid and said process chemistry over said substrate;
   measuring a flow condition that varies with the concentration of said process chemistry in said supercritical fluid flowing past a flow condition measurement device;
   determining a flow rate of said supercritical fluid and process chemistry through said system from a variation of said measured flow condition; and
   recirculating said supercritical fluid through said high pressure processing chamber;
   said determining said flow rate comprising determining a volume of said supercritical fluid circulating through said high pressure processing system, and dividing said volume by a difference in time between a first variation in a signal from said flow condition measurement device as said process chemistry in said supercritical fluid passes said flow condition measurement device a first time and a second variation in said signal from said flow condition measurement device as said process chemistry in said supercritical fluid passes said flow condition measurement device a second time.

2. The method of claim 1, further comprising:
   adjusting said flow rate of said supercritical fluid and said process chemistry according to a difference between said measured value of said flow rate and a target value of said flow rate.

3. The method of claim 1, further comprising:
   adjusting said flow rate of said supercritical fluid in response to the actual flow rate determination.

4. The method of claim 1, further comprising:
   determining the homogeneity of said supercritical fluid as a result of the flow rate determination; and
   timing the said flowing of said supercritical fluid and said process chemistry over said substrate in response to the homogeneity determination.

5. The method of claim 1, wherein said flow condition measurement device is selected from a group which consists of at least one coriolis meter, at least one turbidity meter, or a combination thereof.

6. The method of claim 1, wherein said measuring a flow condition further comprises;
   measuring the homogeneity of said process chemistry in said supercritical fluid, wherein said supercritical fluid is flowing through a recirculation loop bypassing said high pressure processing chamber prior to flowing said supercritical fluid and said process chemistry over said substrate.

7. The method of claim 1, wherein said determining said flow rate further comprises:
   using two or more turbidity meters, whereby the distance between said turbidity meters is known and the time difference between a first time associated with the passing of a flow disturbance by a first turbidity meter and a second time associated with the passing of said flow disturbance by a second turbidity meter is utilized to determine said flow rate.

8. The method of claim 1, wherein the volume ratio of said process chemistry to said supercritical fluid is within the range of from about 1 to 15 v/v %.

9. The method of claim 1, wherein said introducing a process chemistry further comprises:
selecting said process chemistry from the group consisting of chemicals used for solvents, co-solvents, surfactants, etchants, acids, bases, chelators, oxidizers, film-forming precursors, or reducing agents, or any combination thereof.

10. The method of claim 1, wherein said substrate consists of semiconductor material, metallic material, dielectric material, ceramic material, or polymer material, or a combination of two or more thereof.

11. The method of claim 10, wherein said forming a supercritical fluid is accomplished by selecting said fluid from the group consisting of carbon dioxide, oxygen, argon, krypton, xenon, ammonia, methane, methanol, dimethyl ketone, hydrogen, water, and sulfur hexafluoride.

12. The method of claim 11, wherein said introducing a process chemistry further comprises:
selecting said process chemistry from the group consisting of chemicals used for solvents, co-solvents, surfactants, etchants, acids, bases, chelators, oxidizers, film-forming precursors, or reducing agents, or any combination thereof.

13. The method of claim 12, wherein the volume ratio of said process chemistry to said supercritical fluid is within the range of from about 1 to 15 v/v %.

14. The method of claim 13, wherein said measuring a flow condition further comprises;
measuring the homogeneity of said process chemistry in said supercritical fluid, wherein said process chemistry and said supercritical fluid are flowing through a recirculation loop bypassing said high pressure processing chamber prior to flowing said process chemistry in said supercritical fluid over said substrate.

15. A method of treating a substrate comprising:
placing said substrate in a high pressure processing chamber of a high pressure processing system onto a platen configured to support said substrate;
forming a supercritical fluid from a fluid by adjusting a pressure of said fluid above the critical pressure of said fluid, and adjusting a temperature of said fluid above the critical temperature of said fluid;
introducing said supercritical fluid to said high pressure processing chamber;
introducing a process chemistry to said supercritical fluid;
flowing said supercritical fluid and said process chemistry over said substrate;
measuring a flow condition that varies with the concentration of said process chemistry in said supercritical fluid flowing past a flow condition measurement device;
determining a flow rate of said supercritical fluid and process chemistry through said system from a variation of said measured flow condition; and
said measuring a flow condition further comprising measuring the homogeneity of said process chemistry in said supercritical fluid, wherein said supercritical fluid is flowing through a recirculation loop bypassing said high pressure processing chamber prior to flowing said supercritical fluid and said process chemistry over said substrate;
said substrate consists of semiconductor material, metallic material, dielectric material, ceramic material, or polymer material, or a combination of two or more thereof;
said forming a supercritical fluid being accomplished by selecting said fluid from the group consisting of carbon dioxide, oxygen, argon, krypton, xenon, ammonia, methane, methanol, dimethyl ketone, hydrogen, water, and sulfur hexafluoride;
said introducing a process chemistry further comprising selecting said process chemistry from the group consisting of chemicals used for solvents, co-solvents, surfactants, etchants, acids, bases, chelators, oxidizers, film-forming precursors, or reducing agents, or any combination
thereof; the volume ratio of said process chemistry to said supercritical fluid being within the range and including about 1 to 15 v/v %;
said measuring a flow condition further comprising measuring the homogeneity of said process chemistry in said supercritical fluid, wherein said process chemistry and said supercritical fluid are flowing through a recirculation loop bypassing said high pressure processing chamber prior to flowing said process chemistry in said supercritical fluid over said substrate;
said measuring said homogeneity of said process chemistry in said supercritical fluid further comprising determining a mixing time of said process chemistry in said supercritical fluid through said recirculation loop by observing when a difference in signal subsides to a negligible amount, wherein said difference in signal is between a first variation in a signal from said flow condition measurement device as said process chemistry in said supercritical fluid passes said flow condition measurement device a first time and a subsequent variation in said signal from said flow condition measurement device as said process chemistry in said supercritical fluid passes said flow condition measurement device a subsequent time.

16. A method of treating a substrate comprising:
placing said substrate in a high pressure processing chamber of a high pressure processing system onto a platen configured to support said substrate;
forming a supercritical fluid from a fluid by adjusting a pressure of said fluid above the critical pressure of said fluid, and adjusting a temperature of said fluid above the critical temperature of said fluid;
introducing said supercritical fluid to said high pressure processing chamber;
introducing a process chemistry to said supercritical fluid;
flowing said supercritical fluid and said process chemistry over said substrate;
measuring a flow condition that varies with the concentration of said process chemistry in said supercritical fluid flowing past a flow condition measurement device;
determining a flow rate of said supercritical fluid and process chemistry through said system from a variation of said measured flow condition; and
said measuring a flow condition further comprising measuring the homogeneity of said process chemistry in said supercritical fluid, wherein said supercritical fluid is flowing through a recirculation loop bypassing said high pressure processing chamber prior to flowing said supercritical fluid and said process chemistry over said substrate;

said measuring said homogeneity of said process chemistry in said supercritical fluid comprising:

determining a volume of said supercritical fluid circulating through said recirculation loop, and dividing said volume by a difference in time between a first variation in a signal from said flow condition measurement device as said process chemistry in said supercritical fluid passes said flow condition measurement device a first time and a second variation in said signal from said flow condition measurement device as said process chemistry in said supercritical fluid passes said flow condition measurement device a second time.

* * * * *

UNITED STATES PATENT AND TRADEMARK OFFICE
CERTIFICATE OF CORRECTION

PATENT NO. : 7,435,447 B2  Page 1 of 1
APPLICATION NO. : 11/058327
DATED : October 14, 2008
INVENTOR(S) : Parent It is certified that error appears in the above-identified patent and that said Letters Patent is hereby corrected as shown below:

In Column 6, lines 40-41, "tri-isoprpylamine," should read -- tri-isopropylamine, --.

In Column 8, lines 56-57, "such a methanol" should read -- such as methanol --.

In Column 10, line 46, "flow system 120 increase" should read -- flow system 120 to increase --.

In Column 13, line 42, "a process chemistry comprising is introduced" should read -- a process chemistry is introduced --.

In Claim 6, Column 14, line 57, "condition further comprises;" should read -- condition further comprises: --.

In Claim 14, Column 15, line 37, "condition further comprises;" should read -- condition further comprises: --.

In Claim 15, Column 16, lines 17-18, move placement of the paragraph return to after "thereof;" as follows:
            "combination
      thereof, the volume ratio"

should read:

-- combination thereof;
      the volume ratio --.

Signed and Sealed this

Sixteenth Day of February, 2010

David J. Kappos
*Director of the United States Patent and Trademark Office*